US011873494B2

(12) United States Patent
Green et al.

(10) Patent No.: US 11,873,494 B2
(45) Date of Patent: Jan. 16, 2024

(54) GENETIC AND PHARMACOLOGICAL TRANSCRIPTIONAL UPREGULATION OF THE REPRESSED FXN GENE AS A THERAPEUTIC STRATEGY FOR FRIEDREICH ATAXIA

(71) Applicant: University of Massachusetts, Boston, MA (US)

(72) Inventors: Michael R. Green, Boylston, MA (US); Minggang Fang, Northborough, MA (US)

(73) Assignee: University of Massachusetts, Boston, MA (US)

( * ) Notice: Subject to any disclaimer, the term of this patent is extended or adjusted under 35 U.S.C. 154(b) by 177 days.

(21) Appl. No.: 17/406,441

(22) Filed: Aug. 19, 2021

(65) Prior Publication Data
US 2022/0042023 A1 Feb. 10, 2022

Related U.S. Application Data

(62) Division of application No. 16/487,876, filed as application No. PCT/US2018/018181 on Feb. 14, 2018, now Pat. No. 11,124,795.

(60) Provisional application No. 62/464,557, filed on Feb. 28, 2017.

(51) Int. Cl.
*C07K 14/47* (2006.01)
*C12N 15/113* (2010.01)
*A61K 45/06* (2006.01)

(52) U.S. Cl.
CPC .......... *C12N 15/1137* (2013.01); *C07K 14/47* (2013.01); *A61K 45/06* (2013.01); *C12N 2310/11* (2013.01); *C12N 2310/14* (2013.01)

(58) Field of Classification Search
CPC ........................ C12N 15/1137; C07K 14/47
See application file for complete search history.

(56) References Cited

U.S. PATENT DOCUMENTS

| | | | |
|---|---|---|---|
| 11,124,795 | B2 | 9/2021 | Green et al. |
| 2015/0065522 | A1 | 3/2015 | Albrecht et al. |
| 2016/0201063 | A1 | 7/2016 | Ozsolak |
| 2019/0151289 | A1* | 5/2019 | Yan ...................... A61K 38/415 |
| 2019/0376064 | A1 | 12/2019 | Green et al. |

FOREIGN PATENT DOCUMENTS

| | | |
|---|---|---|
| WO | WO 2014/139326 | 9/2014 |
| WO | WO 2014/164708 | 10/2014 |
| WO | WO 2015/023938 | 2/2015 |

OTHER PUBLICATIONS

Sandi et al., "Epigenetic-based therapies for Friedreich ataxia," Front Genet 2014; 5:165 ("Sandi2"). (Year: 2014).*
Sandi et al., "Epigenetics in Friedreich's Ataxia: Challenges and Opportunities for Therapy," Genetics Research International vol. 2013. (Year: 2013).*
Bradley et al., "Clinical, biochemical and molecular genetic correlations in Friedreich's ataxia. Human molecular genetics," Jan. 22, 2000, 9(2):275-82.
Bürk et al., "Monitoring progression in Friedreich ataxia (FRDA): the use of clinical scales." *Journal of Neurochemistry*, 126 (2013): 118-124.
Burridge et al., "A universal system for highly efficient cardiac differentiation of human induced pluripotent stem cells that eliminates interline variability," PloS one, Apr. 8, 2011, 6(4):e18293, 16 pages.
Busskamp et al., "Rapid neurogenesis through transcriptional activation in human stem cells," Molecular Systems Biology, Nov. 1, 2014, 10(11), 22 pages.
Campuzano et al., "Friedreich's ataxia: autosomal recessive disease caused by an intronic GAA triplet repeat expansion," Science, Mar. 8, 1996, 271(5254):1423-7.
Chutake et al., "Epigenetic promoter silencing in Friedreich ataxia is dependent on repeat length." Annals of Neurology, Oct. 2014, 76(4):522-8.
Codazzi et al., "Friedreich ataxia-induced pluripotent stem cell-derived neurons show a cellular phenotype that is corrected by a benzamide HDAC inhibitor," Human Molecular Genetics, Nov. 15, 2016, 25(22):4847-55.
Dell'Era et al., "Cardiac disease modeling using induced pluripotent stem cell-derived human cardiomyocytes," World Journal of Stem Cells, Mar. 26, 2015, 7(2):329.
Divakaruni et al., "Analysis and interpretation of microplate-based oxygen consumption and pH data," InMethods in Enzymology, Academic Press, Jan. 1, 2014, 547:309-54.
Foury et al., "Deletion of the yeast homologue of the human gene associated with Friedreich's ataxia elicits iron accumulation in mitochondria, " FEBS Letters, Jul. 14, 1997, 411(2-3):373-7.
Harding et al., "'Pseudo-dominant' inheritance in Friedreich's ataxia," Journal of Medical Genetics, Aug. 1, 1981, 18(4):285-7.
He et al., "The EED protein-protein interaction inhibitor A-395 inactivates the PRC2 complex," Nature Chemical Biology, Apr. 2017, 13(4), 10 pages.
Kim et al., "Targeted disruption of the EZH2-EED complex inhibits EZH2-dependent cancer," Nature Chemical Biology, Oct. 2013, 9(10):643-50.
Koeppen et al., "The dentate nucleus in Friedreich's ataxia: the role of iron-responsive proteins," Acta Neuropathologica, Aug. 1, 2007, 114(2):163-73.

(Continued)

*Primary Examiner* — Jared Barsky
(74) *Attorney, Agent, or Firm* — Fish & Richardson P.C.

(57) ABSTRACT

Methods of treating subjects having disorders associated with mutations in the FXN gene and/or having reduced expression of frataxin protein, e.g., Friedreich ataxia (FA). Generally, the methods include administering a therapeutically effective amount of an agent that increases expression of frataxin protein as described herein, e.g., an inhibitor of a FXN Repressing Factor (FXN-RF).

7 Claims, 24 Drawing Sheets

(56) References Cited

OTHER PUBLICATIONS

Ku et al., "Friedreich's ataxia induced pluripotent stem cells model intergenerational GAA · TTC triplet repeat instability," Cell Stem Cell, Nov. 5, 2010, 7(5):631-7.
Li et al., "Excision of expanded GAA repeats alleviates the molecular phenotype of Friedreich's ataxia, " Molecular Therapy, Jun. 1, 2015, 23(6):1055-65.
McAllister et al., "Recent progress in histone demethylase inhibitors," Journal of Medicinal Chemistry, Feb. 2, 2016, 59(4):1308-29.
Pandolfo, "Friedreich ataxia," Archives of Neurology, Oct. 13, 2008, 65(10):1296-303.
PCT International Preliminary Report on Patentability in International Appln. No. PCT/US18/18181, dated Sep. 3, 2019, 9 pages.
PCT International Search Report and Written Opinion in International Appln. No. PCT/US18/18181, dated Jun. 21, 2018, 16 pages.
Pianese et al., "Real time PCR quantification of frataxin mRNA in the peripheral blood leucocytes of Friedreich ataxia patients and carriers," Journal of Neurology, Neurosurgery & Psychiatry, Jul. 1, 2004, 75(7):1061-3.
Plasterer et al., "Development of frataxin gene expression measures for the evaluation of experimental treatments in Friedreich's ataxia," PLoS One, May 17, 2013, 8(5):e63958, 9 pages.
Qi et al., "An allosteric PRC2 inhibitor targeting the H3K27me3 binding pocket of EED," Nature Chemical Biology, Apr. 2017, 13(4):381, 11 pages.
Rai et al., "Two new pimelic diphenylamide HDAC inhibitors induce sustained frataxin upregulation in cells from Friedreich's ataxia patients and in a mouse model," PloS one, Jan. 21, 2010, 5(1):e8825, 1-8.
Sandi et al., "Epigenetic-based therapies for Friedreich ataxia, " frontiers in Genetics, Jun. 3, 2014.
Sandi et al., "Prolonged treatment with pimelic o-aminobenzamide HDAC inhibitors ameliorates the disease phenotype of a Friedreich ataxia mouse model," Neurobiology of Disease, Jun. 1, 2011, 42(3):496-505.
Sharma et al., "Friedreich ataxia in carriers of unstable borderline GAA triplet-repeat alleles," Annals of Neurology: Official Journal of the American Neurological Association and the Child Neurology Society, Dec. 2004, 56(6):898-901.
Sheridan et al., "Epigenetic characterization of the FMR1 gene and aberrant neurodevelopment in human induced pluripotent stem cell models of fragile X syndrome," PloS one, Oct. 12, 2011, 6(10):e26203, 13 pages.
Urrutia et al., "The interplay between iron accumulation, mitochondrial dysfunction, and inflammation during the execution step of neurodegenerative disorders," Frontiers in Pharmacology, Mar. 10, 2014, 5:38.
Wajapeyee et al., "Oncogenic RAS directs silencing of tumor suppressor genes through ordered recruitment of transcriptional repressors," Genes & Development, Oct. 15, 2013, 27(20):2221-6.
Waldvogel et al., "Increased iron in the dentate nucleus of patients with Friedreich's ataxia," Annals of Neurology, Jul. 1999, 46(1):123-5.
Willis et al., "Lateral-flow immunoassay for the frataxin protein in Friedreich's ataxia patients and carriers," Molecular Genetics and Metabolism, Aug. 1, 2008, 94(4):491-7.
Wong et al., "The Friedreich's ataxia mutation confers cellular sensitivity to oxidant stress which is rescued by chelators of iron and calcium and inhibitors of apoptosis," Human Molecular Genetics, Mar. 1, 1999, 8(3):425-30.

* cited by examiner

F2880-2566

F5564-0146

F6235-0533

F3407-3748

F0307-0365

F3407-0197

F6196-0976

F3095-0357

GENETIC AND PHARMACOLOGICAL TRANSCRIPTIONAL UPREGULATION OF THE REPRESSED FXN GENE AS A THERAPEUTIC STRATEGY FOR FRIEDREICH ATAXIA

CROSS REFERENCE TO RELATED APPLICATION

This application is a divisional application of and claims priority under 35 U.S.C. § 121 to U.S. application Ser. No. 16/847,876, filed Aug. 22, 2019, which is the national phase application under 35 U.S.C. § 371 of PCT/US2018/018181, filed Feb. 14, 2018, which claims the benefit of priority under 35 U.S.C. § 119(e) to U.S. Application No. 62/464,557 filed Feb. 28, 2017. The entire contents of the foregoing are incorporated herein by reference.

TECHNICAL FIELD

Described herein are methods of treating subjects with disorders associated with mutations in the FXN gene and that have reduced expression of frataxin protein, e.g., Friedreich ataxia (FA). Generally, the methods include administering a therapeutically effective amount of an agent that increases expression of frataxin protein as described herein, e.g., an inhibitor of a FXN Repressing Factor (FXN-RF).

BACKGROUND

Friedreich ataxia (also called Friedreich's ataxia) (FA) is an autosomal recessive inherited disease that causes progressive damage to the nervous system, resulting in movement problems. FA is the most common genetic form of ataxia, and occurs in approximately 1 in 50,000 people. Symptoms typically first appear at 5-15 years of age, followed by progressive neurodegeneration. Typically, within 10 years following the onset of symptoms, the patient is wheelchair bound. The disease affects multiple organs, including the heart and pancreas. Patients have a shortened life expectancy, with most patients dying of cardiac failure. To date, there is no effective therapy for FA.

FA is caused by a GAA•TTC triplet repeat expansion in the first intron of the FXN gene (also called the triplet repeat expansion (TRE)-FXN gene NCBI RefSeqGene NG_008845.2), which encodes a protein called frataxin, a ubiquitous, nuclear-encoded mitochondrial protein (Campuzano et al. 1996, *Science* 271:1423-1427). Unaffected individuals have 6-30 GAA•TTC repeats, whereas affected individuals have approximately 70-1000 repeats (Sharma et al. 2004, *Ann Neurol* 56:898-901; Pandolfo 2008, *Arch Neurol* 65:1296-1303). The effect of the GAA•TTC repeat expansion mutation is to repress FXN expression at the level of transcription. The extent of FXN repression is directly related to the length of the GAA•TTC repeat; age of onset and disease severity are also correlated with the length of the GAA•TTC repeat (Chutake et al. 2014, *Ann Neurol* 76:522-528). Importantly, the TRE-FXN gene encodes functional frataxin, albeit at reduced levels. Transcriptional upregulation of the TRE-FXN gene is a potential therapeutic strategy for treating FA.

SUMMARY

Our work has identified a number of factors including biologicals and small molecule inhibitors that increase transcription of the TRE-FXN gene. For example, described herein are compounds that increase transcription of the TRE-FXN gene, which has immediate therapeutic implications.

Provided herein are methods for treating a subject having a disorder associated with a mutation in the FXN gene and having reduced expression of frataxin protein. The methods include administering to the subject a therapeutically effective amount of a small molecule inhibitor of a FXN Repressing Factor (FXN-RF), e.g., selected from the group consisting of DNMT3A, DNMT3B, SETDB1, EZH2, EED, EHMT2/G9a, RING1B/RNF2, KDMSA, KDMSD, HDAC2, HDAC5, and SIRT7. Exemplary small molecules include molecules shown in Table 1 or FIGS. 7A-7F.

Alternatively, or in addition, the methods can include administering to the subject a therapeutically effective amount of an inhibitory nucleic acid that targets and specifically reduces expression of a FXN Repressing Factor (FXN-RF) selected from the group consisting of DNMT3A, DNMT3B, EED, EZH2, SETDB1, EHMT2/G9a, RING1B/RNF2, KDMSA, KDMSD, HDAC2, HDAC5, and SIRT7. In some embodiments, the inhibitory nucleic acid is a small interfering RNA, small hairpin RNA, or antisense oligonucleotide.

Also provided herein is the use of a small molecule inhibitor of a FXN Repressing Factor (FXN-RF) selected from the group consisting of EZH2, SETDB1, DNMT3A, DNMT3B, SETDB1, EED, EHMT2/G9a, RING1B/RNF2, KDMSA, KDMSD, HDAC2, HDAC5, and SIRT7, optionally a molecule shown in Table 1 or FIGS. 7A-7F, for treating a subject having a disorder associated with a mutation in the FXN gene and having reduced expression of frataxin protein. Also provided is the use of an inhibitory nucleic acid that targets and specifically reduces EZH2, SETDB1, DNMT3A, DNMT3B, SETDB1, EED, EHMT2/G9a, RING1B/RNF2, KDMSA, KDMSD, HDAC2, HDAC5, and SIRT7, e.g., a small interfering RNA, small hairpin RNA, or antisense oligonucleotide, for treating a subject having a disorder associated with a mutation in the FXN gene and having reduced expression of frataxin protein.

In some embodiments, the subject has Friedreich ataxia (FA).

In some embodiments, the small molecule is an inhibitor as shown in Table 1, e.g., an inhibitor of EZH2 (e.g., EPZ6438, GSK126, F2880-2566; F5564-0146; F6235-0533; or F3407-3748); an inhibitor of SETDB1 and EHMT2 (e.g., chaetocin); an inhibitor of KDMSA (e.g., F3222-4242; F3358-0326; or F3385-1519) or KDMSD; an HDAC inhibitor (e.g., F0307-0365; F3407-0197; F6196-0976; F3095-0357; LMK235; PCI-24781; or trichostatin A (TSA)); an inhibitor of SUV39H1 (e.g., F2470-0099; F2880-1734; or F3222-4478); an inhibitor of DNMT3A or DNMT3B (e.g., F2578-0281; F3258-0176; or F3342-0131); or an inhibitor of SIRT7 (e.g., F2721-0219; F3220-0531; F3220-0613; F3319-0778; or F3385-2786). In place of an inhibitor of EZH2, other inhibitors of components of the PRC2 complex can be used, e.g., inhibitors of EED In some embodiments, the small molecule inhibitors of FXN-RF is not an HDAC inhibitor, or is not an inhibitor of HDAC1 or HDAC3, or is not RGFP109 as described in Plasterer et al., *PLoS One*. 2013; 8(5): e63958, and/or is not compounds 106 (N1-(2-aminophenyl)-N7-p-tolylheptanediamide), 136 (N-(6-(2-amino-4-fluorophenylamino)-6-oxyhexyl)-4-methylbenzamide), or 109 (N-(6-(2-aminophenylamino)-6-oxyhexyl)-4-methylbenzamide) described in Rai et al., *PLoS One*. 2010; 5(1): e8825 and Sandi et al., *Neurobiol Dis*. 2011 June; 42(3): 496-505.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A shows a quantitative RT-PCR (qRT-PCR) analysis monitoring expression of the TRE-FXN gene in an iPSC line (GM23404) derived from a patient with FA (hereafter called FA(GM23404) iPSCs) expressing one of two unrelated shRNAs targeting a set of 33 epigenetic repressors. The results were normalized to that obtained with a control non-silencing (NS) shRNA, which was set to 1. The results identified 10 FXN repressing factors (FXN-RFs). FIG. 1B shows an immunoblot analysis showing frataxin levels in FA(GM23404) iPSCs expressing an NS or a FXN-RF shRNA. Frataxin levels in normal iPSCs are shown. α-tubulin (TUBA) was monitored as a loading control. The results allow us to show that knockdown of each FXN-RF increases frataxin to levels comparable to that observed in normal iPSCs. FIG. 1C shows qRT-PCR analysis monitoring FXN transcription in a second FA iPSC line, FA(GAA-intact) iPSCs. The results were normalized to that obtained with isogenic FA(GAA-excised) iPSCs, which was set to 1.

FIG. 1D shows chromatin immunoprecipitation (ChIP) analysis monitoring binding of FXN-RFs to the first intron of the TRE-FXN gene, or as a negative control the promoter of the APRT gene, in FA(GM23404) and normal iPSCs. The results were normalized to that obtained with IgG, which was set to 1. FIGS. 1E-1F show ChIP analysis monitoring binding of representative FXN-RFs in FA(GM23404) iPSCs following knockdown of each of the other FXN-RFs. FIG. 1G shows a schematic of a hypothesized ordered pathway of FXN-RF recruitment. Data are represented as mean±SD (n=3 technical replicates of a representative experiment (out of 3 independent experiments)). *P<0.05, **P<0.01.

FIG. 1H shows qRT-PCR analysis monitoring FXN transcription in FA(GM23404) iPSCs treated with EPZ6438 (0.2 µM), GSK126 (0.1 µM), chaetocin (0.1 µM), LMK235 (0.5 µM), PCI-24781 (0.2 µM), TSA (10 nM), KDM5Ai (1 µM) or, as a control, DMSO. The results were normalized to that obtained in normal iPSCs, which was set to 1. FIG. 1I shows qRT-PCR analysis monitoring FXN transcription in FA(GM23404) iPSCs treated with GSK126 (0.01, 0.1, 1 µM), TSA (1, 10, 100 nM) or KDM5Ai (0.1, 1, 10 µM). The results were normalized to that obtained with DMSO, which was set to 1. FIG. 1J shows the results of immunoblot analysis showing frataxin levels in FA(GM23404) iPSCs treated with a small molecule FXN-RF inhibitor. FIG. 1K shows qRT-PCR analysis monitoring FXN transcription in FA(GAA-intact) iPSCs. Data are represented as mean±SD (n=3 technical replicates of a representative experiment (out of 3 independent experiments)). *P<0.05, **<0.01.

FIG. 2A is a micrograph showing morphology of neurons derived from FA(GM23404) iPSCs, by immunofluorescence with an anti-TUJ1 antibody. FIG. 2B shows the percentage of TUJ1-positive (left) and phosphorylated histone H3 at serine 10 (pH3)-positive (right) in FA iPSCs and FA neurons. FIG. 2C shows qRT-PCR analysis monitoring FXN transcription in FA neurons expressing an shRNA targeting an FXN-RF. The results were normalized to that obtained in normal neurons, which was set to 1. These results include normal neurons as controls, to show that upon reactivation, FXN levels increase to levels comparable to that observed in normal neurons. FIG. 2D shows immunoblot analysis showing frataxin levels in FA neurons expressing an NS or FXN-RF shRNA. Frataxin levels in normal neurons are shown. FIG. 2E shows qRT-PCR analysis monitoring FXN transcription in FA neurons treated with small molecule FXN-RF inhibitors. FIG. 2F shows immunoblot analysis showing frataxin levels in FA neurons treated with a small molecule FXN-RF inhibitor. Data are represented as mean±SD (n=3 technical replicates of a representative experiment (out of 3 independent experiments)). *P<0.05, **<0.01.

FIG. 3A shows a representative flow cytometry analysis of FA neurons expressing a non-silencing (NS), EZH2 or HDAC5 shRNA. The neurons were harvested, stained with MitoSOX and analyzed by flow cytometry. FIG. 3B shows quantification of flow cytometry analysis of normal neurons and FA neurons expressing an FXN-RF shRNA or treated with a small molecule FXN-RF inhibitor and stained with MitoSOX. The results were normalized to that obtained with a control NS shRNA, which was set to 1. FIG. 3C shows analysis of oxygen consumption rate in normal neurons and FA neurons expressing an FXN-RF shRNA or treated with a small molecule FXN-RF inhibitor. Data are represented as mean±SD (n=3 technical replicates of a representative experiment (out of 3 independent experiments)). *P<0.05, **<0.01.

FIG. 4A shows the results of analysis of micrographs showing cardiac troponin T (cTNT)- or sarcomeric actinin (SA)-positive cardiomyocytes (CMCs) derived from FA(GM23404) iPSCs. Shown is the percentage of cells staining positive for cTNT or SA in FA iPSCs or FA CMCs. FIG. 4B shows qRT-PCR analysis monitoring FXN transcription in FA CMCs expressing an shRNA targeting an FXN-RF. The results were normalized to that obtained in normal CMCs, which was set to 1. FIG. 4C shows immunoblot analysis showing frataxin levels in FA CMCs expressing an NS or FXN-RF shRNA. Frataxin levels in normal CMCs are shown. FIG. 4D shows qRT-PCR analysis monitoring FXN transcription in FA CMCs treated with small molecule FXN-RF inhibitors. FIG. 4E shows immunoblot analysis showing frataxin levels in FA CMCs treated with a small molecule FXN-RF inhibitor. Data are represented as mean±SD (n=3 technical replicates of a representative experiment (out of 3 independent experiments)). *P<0.05, **<0.01

FIG. 5A shows quantification of flow cytometry analysis of normal cardiomyocytes (CMCs) and FA CMCs expressing an FXN-RF shRNA or treated with a small molecule FXN-RF inhibitor and stained with MitoSOX. The results were normalized to that obtained with a control NS shRNA, which was set to 1. FIG. 5B shows analysis of oxygen consumption rate in normal CMCs and FA CMCs expressing an FXN-RF shRNA or treated with a small molecule FXN-RF inhibitor. Data are represented as mean±SD (n=3 technical replicates of a representative experiment (out of 3 independent experiments)). *P<0.05, **<0.01.

DETAILED DESCRIPTION

Figure 1A:
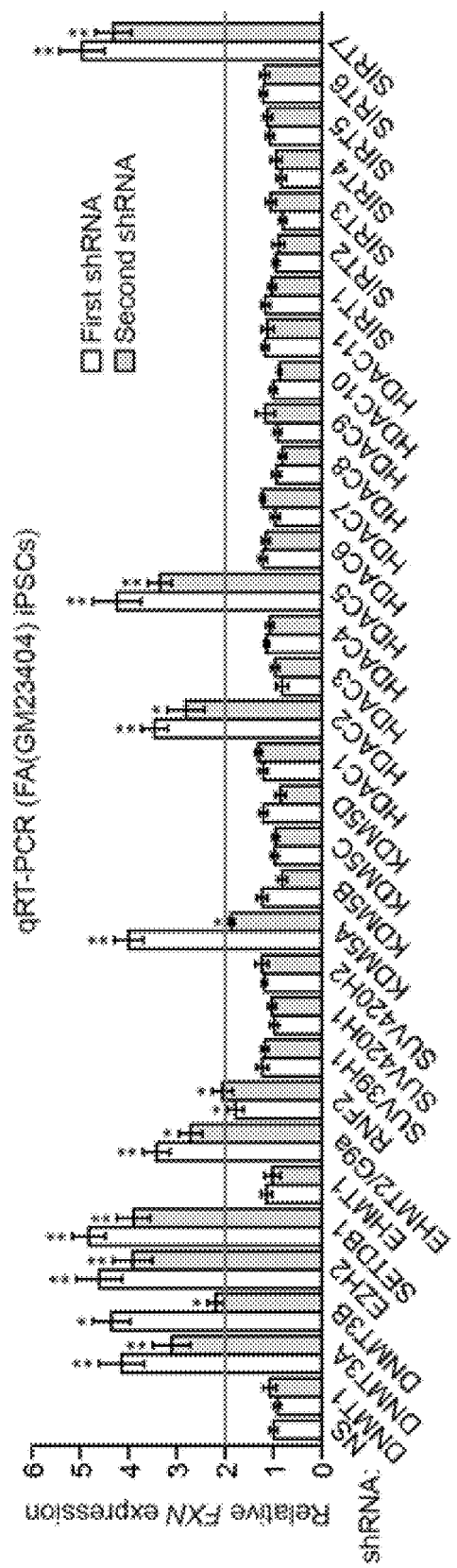
FIGS. 1A-1C show identification of epigenetic repressors that promote repression of FXN in FA induced pluripotent stem cells (iPSCs).

FA is caused by transcriptional repression of the TRE-FXN gene, resulting in decreased levels of frataxin. The deficiency of frataxin is associated with several indicators of mitochondrial dysfunction, including iron accumulation in the mitochrondria, impairment of iron-sulfur (Fe—S) cluster-containing enzymes, increased sensitivity to oxidative stress, and deficits of respiratory chain complex activities (Bradley et al. 2000, *Hum Mol Genet* 9:275-282; Foury and Cazzalini 1997, *FEBS Lett* 411:373-377; Waldvogel et al. 1999, *Ann Neurol* 46:123-125; Koeppen et al. 2007, *Acta Neuropathol* 114:163-173; Wong et al. 1999, *Hum Mol Genet* 8:425-430).

Recent studies have shown that several repressive epigenetic marks, comprising chemical modifications of DNA and histones, are associated with repression of the TRE-FXN gene, including increased DNA methylation, histone H3 lysine 27 trimethylation (H3K27me3), histone H3 lysine 9 trimethylation (H3K9me3), and histone H4 lysine 20 trimethylation (H4K20me3) (reviewed in Sandi et al. 2014, *Front Genet* 5:165). Conversely, there is a decrease in activating marks, including histone (H2A/2B/3/4) acetylation and histone H3 lysine 4 trimethylation (H3K4me3).

Transcriptional upregulation of the TRE-FXN gene is a potential therapeutic strategy for treating FA. An attractive feature of this approach is that it is based on correcting the root cause of the disease, the decreased levels of frataxin, rather than some secondary, downstream consequence of the frataxin deficiency. Notably, the level of frataxin in FA patients is only a few-fold lower than that in asymptomatic carriers, who harbor one TRE-FXN allele and one normal FXN allele (Pianese et al. 2004, *J Neurol* Neurosurg Psychiatr 75:1061-1063). Thus, even a modest increase in transcription of the TRE-FXN gene is likely to be therapeutically beneficial.

The epigenetic regulators responsible for depositing repressive marks or for removing activating marks are attractive targets to upregulate transcription of the TRE-FXN gene. Indeed, previous studies have evaluated histone deacetylase (HDAC) inhibitors as potential FA therapeutics (Rai et al. 2010, *PLoS One* 5:e8825; Sandi et al. 2011, *Neurobiol Dis* 42:496-505; Plasterer et al., *PLoS One*. 2013; 8(5): e63958). Although these HDAC inhibitors upregulate transcription of the TRE-FXN gene and ameliorate disease phenotypes in an FA mouse model, they suffer from non-specificity and toxicity. To date, there has been no systematic attempt to identify additional negative epigenetic regulators of FXN, which may provide more desirable therapeutic targets.

As demonstrated herein, there are a number of negative epigenetic regulators whose pharmacological inhibition will lead to increased transcription of the TRE-FXN gene, resulting in increased frataxin levels and decreased disease symptomatology. The present methods include inhibiting, e.g., either through inhibitory nucleic acids (e.g., RNA interference (RNAi)-mediated knockdown) or small molecule inhibitors, these epigenetic repressors of the TRE-FXN gene. In some embodiments, the inhibition of these repressors increases transcription of the TRE-FXN gene at least 2-6-fold or more.

Methods of Treatment

The methods described herein include methods for the treatment of disorders associated with mutations in the FXN gene and/or that have reduced expression of frataxin protein (but wherein the frataxin protein itself is functional). In some embodiments, the disorder is Friedreich ataxia (FA). Generally, the methods include administering a therapeutically effective amount of an agent that increases levels of frataxin protein as described herein, to a subject who is in need of, or who has been determined to be in need of, such treatment. Methods known in the art can be used to diagnose or identify a subject as having a disorder associated with a mutation in the FXN gene that reduces expression of the frataxin protein, e.g., sequencing or identification of the presence of trinucleotide repeat expansion (e.g., using a commercially available assay such as the Friedreich ataxia (FXN) Repeat Expansion Test (Athena Diagnostics)); a quantitative immunoassay to measure frataxin levels, e.g., as described in Plasterer et al., *PLoS One*. 2013; 8(5): e63958, or a lateral flow test as described in Willis et al., *Mol Genet Metab*. 2008 August; 94(4): 491-497 or commercially available kits such as the dipstick kit from abcam (ab109881); MRI to detect atrophy of the cervical spinal cord with minimal evidence of cerebellar atrophy; transcranial sonography for assessment of both cerebellar and noncerebellar abnormalities, e.g., dentate hyperechogenicity. Typically, subjects present with gait ataxia (e.g., tabetocerebellar gait), with ataxia progressing to the legs, trunk, and arms; development of tremors; titubation; and trembling. To determine severity, any of three scales can be used, e.g., The International Cooperative Ataxia Rating Scale (ICARS), the Friedreich Ataxia Rating Scale (FARS), and the Scale for the Assessment and Rating of Ataxia (SARA), see, e.g., Burk et al., *J. Neurochem.* 126 Suppl. 1:118-24 (2013).

As used in this context, to "treat" means to ameliorate at least one symptom of the disorder associated with mutations in the FXN gene that reduce expression. FA is an autosomal recessive neurodegenerative disorder that results in progressive gait and limb ataxia with associated limb muscle weakness, absent lower limb reflexes, extensor plantar responses, dysarthria, and decreased vibratory sense and proprioception, as well as cardiac manifestations including cardiac dysfunction and heart failure; visual field defects; and diabetes. Thus, a treatment can result in a reduction in the severity of these deficits or a reduction in the rate of decline or degeneration. Administration of a therapeutically effective amount of a compound described herein for the treatment of a condition associated with mutations in the FXN gene that reduce expression, e.g., FA, will result in improvement in one or more symptoms, e.g., reduction in the severity or rate of decline in gait and limb ataxia, limb muscle weakness, deficits in lower limb reflexes, extensor plantar responses, dysarthria, and vibratory sense and proprioception, and a return or approach to normal gait and limb movements, a return or approach to normal muscle strength and reflexes, a return or approach to normal (flexor) plantar responses, reduced dysarthria/improved speech, and a return or approach to normal vibratory sense and proprioception, as well as a reduction in the severity or risk of cardiac dysfunction and/or heart failure or diabetes. In some embodiments, the treatment results in decreased morbidity or mortality, e.g., a delayed loss of ambulation, an increased life span (average age of death is 37.7±14.4 years, range 21-69, Harding et al., *J. Med Genet.* 18(4):285-7 (1981)) and/or an improved quality of life.

Therapeutic Agents

Agents that increase expression of frataxin protein as described herein include inhibitors of DNMT3A, DNMT3B, EED, EZH2, SETDB1, EHMT2/G9a, RING1B/RNF2, KDM5s, e.g., KDM5A or KDM5D, HDACs, e.g., HDAC2 or HDAC5, EED, or SIRTs, e.g., SIRT5 or SIRT7; these factors are referred to herein as FXN Repressing Factors (FXN-RFs). The agents can include inhibitory nucleic acids and small molecule inhibitors.

Small Molecule Inhibitors or FXN-RFs

A number of small molecule inhibitors of FXN-RFs are known in the art, including those shown in Table 1, many of which are commercially available.

TABLE 1

SMALL MOLECULE INHIBITORS OF FXN REPRESSING FACTORS

| Gene Name | Symbol | Small Molecule Inhibitor |
|---|---|---|
| enhancer of zeste 2 polycomb repressive complex 2 subunit | EZH2 | EPZ6438, GSK126, GSK343, DZNep, EI1, EPZ005678, UNC1999, 3-deazaneplanocin A hydrochloride, EPZ-6438 (tazemetostat) |
| SET domain bifurcated 1 | SETDB1 | chaetocin |
| euchromatic histone lysine methyltransferase 2 | EHMT2 | chaetocin, BIX-01294 |
| lysine demethylase 5A | KDM5A | HDM inhibitor, 2,4-PDCA; JIB04; pyrazole derivative KDM5A inhibitors described in WO2015135094 (referred to herein as KDM5Ai), as well as compounds 65, 90-94, 4-Carboxy-2-heterocyclic pyridine derivatives (e.g., compounds 95-97), pyrazole derivatives (99-123), and others as described in McAllister et al., "Recent Progress in Histone Demethylase Inhibitors," J Med Chem. 2016 Feb 25;59(4):1308-29, as well as compounds described in WO2014164708, WO2014139326, and US20150065522 |
| DNA methyltransferase 3 alpha | DNMT3A | SGI-1027 |
| DNA methyltransferase 3 beta | DNMT3B | SGI-1027 |
| embryonic ectoderm development | EED | EED226 (Qi et al., Nat Chem Biol. 2017 Jan 30); A395 (He et al., Nat Chem Biol. 2017 Jan 30) |
| ring finger protein 2 | RNF2 | PRT4165 |
| histone deacetylase 2 | HDAC2 | LMK235, PCI-24781, TSA, MC 1293, MGCD0103, 4SC-202, CI-994, TC-H 106, Santacruzamate A (CAY10683), mocentinostat (MGCD0103), sodium valproate, BG45 |
| histone deacetylase 5 | HDAC5 | LMK235, PCI-24781, TSA, MC1568, dacinostat, TMP269, |
| sirtuin 7 | SIRT7 | 6-Chloro-2,3,4,9-tetrahydro-1H-carbazole-1-carboxamide, sirtinol |

In some embodiments, the small molecule inhibitors of FXN-RF is not an HDAC inhibitor, or is not an inhibitor of HDAC1 or HDAC3, or is not RGFP109, is not compounds 106 (N1-(2-aminophenyl)-N7-p-tolylheptanediamide), 136 (N-(6-(2-amino-4-fluorophenylamino)-6-oxyhexyl)-4-methylbenzamide), or 109 (N-(6-(2-aminophenylamino)-6-oxyhexyl)-4-methylbenzamide) described in Rai et al., *PLoS One*. 2010; 5(1): e8825 and Sandi et al., *Neurobiol Dis.* 2011 June; 42(3): 496-505.

In addition, peptide-based inhibitors can be used, e.g., EZH2 inhibitor SAH-EZH2, which are hydrocarbon-stapled peptides that mimic the α-helical EED binding domain of EZH2 (residues 40-68) to disrupt the protein interaction between EZH2 and EED). See, e.g., Kim et al., *Nat Chem Biol.* 2013 October; 9(10):643-50. EZH2 is a component of a multi-subunit complex called Polycomb Repressor Complex 2 (PRC2). The other subunits of PRC2 are EED, SUZ12 and RbAp48. The finding that inhibition of EZH2 increases transcription of the TRE-FXN suggests that inhibition of other PRC2 subunits, in particular EED for which small molecule inhibitors are available, would have a similar effect.

Inhibitory Nucleic Acids

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics that specifically hybridize to at least a portion of a target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

The following Table 2 provides exemplary target sequences for the FXN-RFs described herein:

TABLE 2

FXN REPRESSING FACTORS

| Gene Name | Symbol | NCBI RefSeq Acc. No.-Homo sapiens (nucleic acid) |
|---|---|---|
| DNA methyltransferase 3 alpha | DNMT3A | NM_022552.4-isoform a<br>NM_153759.3-isoform b<br>NM_001320892.1-isoform c<br>NM_001320893.1-isoform d |
| DNA methyltransferase 3 beta | DNMT3B | NM_006892.3-isoform 1<br>NM_175848.1-isoform 2<br>NM_175849.1-isoform 3<br>NM_175850.2-isoform 6<br>NM_001207055.1-isoform 7<br>NM_001207056.1-isoform 8 |
| embryonic ectoderm development | EED | NM_003797.4-isoform a<br>NM_001308007.1-isoform c<br>NM_001330334.1-isoform d |
| enhancer of zeste 2 polycomb repressive complex 2 subunit | EZH2 | NM_004456.4-isoform a<br>NM_152998.2-isoform b<br>NM_001203247.1-isoform c<br>NM_001203248.1-isoform d<br>NM_001203249.1-isoform e |
| SET domain bifurcated 1 | SETDB1 | NM_001145415.1-isoform 1<br>NM_012432.3-isoform 2<br>NM_001243491.1-isoform 3 |
| euchromatic histone lysine methyltransferase 2 | EHMT2 | NM_006709.4-isoform a<br>NM_025256.6-isoform b<br>NM_001289413.1-isoform c<br>NM_001318833.1-isoform d |
| ring finger protein 2 | RNF2 | NM_007212.3 |
| lysine demethylase 5A | KDM5A | NM_001042603.2 |
| lysine demethylase 5D | KDM5D | NM_001146705.1-isoform 1<br>NM_004653.4-isoform 2<br>NM_001146706.1-isoform 3 |
| histone deacetylase 2 | HDAC2 | NM_001527.3 |
| histone deacetylase 5 | HDAC5 | NM_005474.4-isoform 1<br>NM_001015053.1-isoform 3 |
| sirtuin 5 | SIRT5 | NM_012241.4-isoform 1<br>NM_031244.3-isoform 2<br>NM_001193267.2-isoform 3<br>NM_001242827.1-isoform 4 |
| sirtuin 7 | SIRT7 | NM_016538.2 |

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required.

Routine methods can be used to design an inhibitory nucleic acid that binds to the target sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., *J. Mol. Biol.*, 1990, 215, 403-410; Zhang and Madden, *Genome Res.*, 1997, 7, 649-656), e.g., using the default parameters.

Once one or more target regions, segments or sites have been identified, e.g., within a target sequence known in the art or provided herein, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a RNA molecule, then the inhibitory nucleic acid and the RNA are considered to be complementary to each other at that position. The inhibitory nucleic acids and the RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the inhibitory nucleic acid and the RNA target. For example, if a base at one position of an inhibitory nucleic acid is capable of hydrogen bonding with a base at the corresponding position of a RNA, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (*Science* 196:180, 1977); Grunstein and Hogness (*Proc. Natl. Acad. Sci.*, USA 72:3961, 1975); Ausubel et al. (*Current Protocols in Molecular Biology, Wiley Interscience*, New York, 2001); Berger and Kimmel (*Guide to Molecular Cloning Techniques*, 1987, *Academic Press*, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., *J. Mol. Biol.*, 1990, 215, 403-410; Zhang and Madden, *Genome Res.*, 1997, 7, 649-656). Inhibitory nucleic acids that hybridize to an RNA can be identified through routine experimentation. In general, the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA. Thus, oligonucleotides are chosen that are sufficiently complementary to the target, i.e., that hybridize sufficiently well and with sufficient specificity, to give the desired effect.

siRNA/Shrna

In some embodiments, the nucleic acid sequence that is complementary to a target RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., *Science* 296:550-553, (2002); Lee et al, *Nature Biotechnol.*, 20, 500-505, (2002); *Miyagishi and Taira, Nature Biotechnol* 20:497-500, (2002); Paddison et al. *Genes & Dev.* 16:948-958, (2002); *Paul, Nature Biotechnol,* 20, 505-508, (2002); *Sui, Proc. Natl. Acad. Sd. USA,* 99(6), 5515-5520, (2002); Yu et al. *Proc Natl Acad Sci USA* 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 *Ann. Rep. Med. Chem.* 30, 285-294; Christoffersen and Marr, 1995 *J. Med. Chem.* 38, 2023-2037). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, *Proc. R. Soc. London, B* 205, 435) have been used to evolve new nucleic acid catalysts capable of catalyzing a variety of reactions, such as cleavage and ligation of phosphodiester linkages and amide linkages, (Joyce, 1989, *Gene,* 82, 83-87; Beaudry et al., 1992, *Science* 257, 635-641; Joyce, 1992, *Scientific American* 267, 90-97; Breaker et al, 1994, *TIBTECH* 12, 268; Bartel et al, 1993, *Science* 261:1411-1418; Szostak, 1993, *TIBS* 17, 89-93; Kumar et al, 1995, *FASEB J.,* 9, 1183; Breaker, 1996, *Curr. Op. Biotech.,* 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $min^{-1}$ in the presence of saturating (10 mM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

Modified Inhibitory Nucleic Acids

In some embodiments, the inhibitory nucleic acids used in the methods described herein are modified, e.g., comprise one or more modified bonds or bases. A number of modified bases include phosphorothioate, methylphosphonate, peptide nucleic acids, or locked nucleic acid (LNA) molecules. Some inhibitory nucleic acids are fully modified, while others are chimeric and contain two or more chemically distinct regions, each made up of at least one nucleotide. These inhibitory nucleic acids typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, ~N(CH3)~O~CH2 (known as a methylene(methylimino) or MMI backbone], CH2-O—N(CH3)-CH2, CH2-N(CH3)-N(CH3)-CH2 and O—N(CH3)-CH2-CH2 backbones, wherein the native phosphodiester backbone is represented as O—P—O—CH,); amide backbones (see De Mesmaeker et al. *Ace. Chem. Res.* 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., *Science* 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, *Biochemistry*, 2002, 41(14), 4503-4510); Genesis, volume 30, issue 3, 2001; Heasman, J., *Dev. Biol.*, 2002, 243, 209-214; Nasevicius et al., *Nat. Genet.*, 2000, 26, 216-220; Lacerra et al., *Proc. Natl. Acad. Sci.*, 2000, 97, 9591-9596; and U.S. Pat. No. 5,034,506, issued Jul. 23, 1991.

Cyclohexenyl nucleic acid oligonucleotide mimetics are described in Wang et al., *J. Am. Chem. Soc.*, 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, $SCH_3$, F, OCN, $OCH_3OCH_3$, $OCH_3O(CH_2)nCH_3$, $O(CH_2)nNH_2$ or $O(CH_2)nCH_3$ where n is from 1 to about 10; Ci to C10 lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-0-$CH_2CH_2OCH_3$, also known as 2'-O-(2-methoxyethyl)] (Martin et al, *Helv. Chim. Acta*, 1995, 78, 486). Other preferred modifications include 2'-methoxy (2'-O-$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. *Nucl. Acids Res.* 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, *Science*, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise *Encyclopedia of Polymer Science and Engineering*', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175, 273; 5, 367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., *Proc. Natl. Acad. Sci.* USA, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al, *Ann. N.Y. Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Mancharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylamino-carbonyl-t oxycholesterol moiety (Crooke et al., *J. Pharmacol. Exp. Ther.*, 1996, 277, 923-937). See also U.S. Pat. Nos. 4,828,979; 4,948,882; 5,218,105; 5,525,465; 5,541,313; 5,545,730; 5,552, 538; 5,578,717; 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241; 5,391, 723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Locked Nucleic Acids (LNAs)

In some embodiments, the modified inhibitory nucleic acids used in the methods described herein comprise locked nucleic acid (LNA) molecules, e.g., including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herein.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA; for example, a series of oligonucleotides of 10-30 nucleotides spanning the length of a target RNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of more than four LNA residues, should be avoided where possible (for example, it may not be possible with very short (e.g., about 9-10 nt) oligonucleotides). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., *Drug Disc. Today* 2(3):287-290 (2005); Koshkin et al., *J. Am. Chem. Soc.,* 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3d ed. (2001); *Current Protocols in Molecular Biology,* Ausubel et al., eds. (John Wiley & Sons, Inc., New York 2010); Kriegler, *Gene Transfer and Expression: A Laboratory Manual* (1990); *Laboratory Techniques In Biochemistry And Molecular Biology: Hybridization With Nucleic Acid Probes, Part I. Theory and Nucleic Acid Preparation,* Tijssen, ed. Elsevier, N.Y. (1993).

Pharmaceutical Compositions

The methods described herein can include the administration of pharmaceutical compositions and formulations comprising inhibitory nucleic acid sequences designed to target an RNA.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy,* 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater. Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; *Remington: The Science and Practice of Pharmacy,* 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as *Remington: The Science and Practice of Pharmacy,* 21st ed., 2005.

Various studies have reported successful mammalian dosing using complementary nucleic acid sequences. For example, Esau C., et al., (2006) *Cell Metabolism,* 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by Krützfeldt J., et al., (2005) *Nature* 438, 685-689, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) *Nature* 452, 896-899, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., compositions for providing cholesterol homeostasis. For example, the inhibitory nucleic acids can be co-administered with drugs for treating or reducing risk of a disorder described herein.

Delivery of siRNA In Vivo

The overall efficacy of RNAi-based therapies depends on the efficiency of the delivery system to selectively target infected or diseased tissue versus normal non-malignant tissue, and on the stability of the agent within the cell. However, since 1998 when the first human RNAi-based clinical trials occurred, the number of clinical trials involving RNAi therapies targeting the liver has rapidly increased (Sehgal, A et al (2013) *J. Hepatology* 59: 1354-1359). To avoid rapid degradation of unmodified siRNAs in the blood and serum in vivo, chemical modification or conjugate formation (simple or poly-) may be used by those skilled in the art. Examples of modifications may include lipid carriers, such as liposomal vehicles (Kanasty, R et al (2013) *Nature Mater.* 12, 967-977); Watanabe et al (2007) *J. Hepatol* 47:744-50; Aleku et al (2008) *Cancer Res* 68:9788-98; Moreira et al (2008) *J. Nanosci Nanotechnol* 8:2187-204; cationic carriers, such as cyclodextrin-based cationic polymers (Heidel et al (2007) *Clin Cancer Res* 13:2207-15) and biodegradable components (Dimitrova et al (2008). In some embodiments, liposome particles (Morrissey, D V et al (2005) *Biotechnol* 23:1002-1007), PEGylated nanoparticles (Carmona, S et al (2009) *Mol Pharm* 6:706-717), or Dynamic PolyConjugate (DPC) (Rozema et al (2007) *PNAS* 104: 12982-12987) may be used to deliver siRNAs to the liver. In some embodiments, this delivery system may feature reversibly masked polymers that are only revealed under specific conditions, such as the acidic environment of the endosome (Rozema et al (2007) *PNAS* 104: 12982-12987). In some embodiments, the delivery system may dependent on the attachment to a liver-specific receptor on the cell surface of hepatocytes, such asialoglycoprotein (Wu, J et al (2002) *Front Biosci* 7:d717-d725). In some embodiments, the target siRNA may directly be conjugated to cholesterol (Wooddell, C et al (2013) *Mol Therapy* 21:973-985). In some embodiments hydrodynamic intravenous injections and electrical pulsing may be used to directly deliver RNAi therapeutics (Morrissey et al (2005) *Hepatology* 41:1349-56; Golzio et al (2005) *Gen Ther* 12:246-51). RNAi therapeutics may also be delivered via electroporation of purified exosomes (Alvarez-Erviti et al (2011) *Nat Biotechnol* 29:341-345). For more information on in vivo delivery of RNAi, please see U.S. Ser. No. 12/479,747; U.S. Pat. Nos. 8,501,930, 8,017,804; 8,357,722; 8,314,227; and 7,371,404.

Pharmaceutical Compositions and Methods of Administration

The methods described herein include the use of pharmaceutical compositions comprising an inhibitor of a FXN Repressing Factor (FXN-RF) as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., Remington: The Science and Practice of Pharmacy, 21st ed., 2005; and the books in the series Drugs and the Pharmaceutical Sciences: A Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

EXAMPLES

The invention is further described in the following examples, which do not limit the scope of the invention described in the claims.

Example 1. Identification of Targets for De-Repressing Tre-Fxn EXPRESSION IN FA IPSCS Factors responsible for depositing repressive marks or for removing activating marks are potential targets to increase transcription of the epigenetically repressed TRE-FXN gene. The following table is a non-comprehensive list of factors responsible for depositing or removing the epigenetic marks on the repressed TRE-FXN gene.

TABLE 3 factors potentially responsible for depositing or removing the epigenetic marks on the repressed TRE-FXN gene

| Epigenetic mark | Potential target(s) |
| --- | --- |
| DNAme | DNMT1, DNMT3A, DNMT3B |
| H3K27me3 | EZH2 |
| H3K9me3 | SETDB1, EHMT1/GLP, EHMT2/G9a, SUV39H1 |
| H4K20me3 | SUV420H1, SUV420H2 |
| H2Aub | RING1B/RNF2 |
| H2A/2B/3/4ac | HDAC1-11, SIRT1-7 |
| H3K4me3 | KDM5A-D |

Figure 1B:
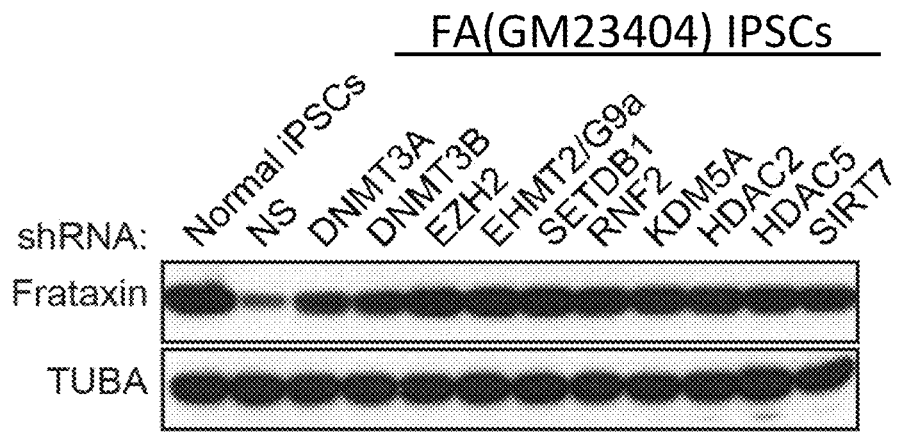

To identify epigenetic regulators that mediate repression of TRE-FXN, we assembled a small-scale shRNA library comprising 162 shRNAs directed against 33 well-characterized epigenetic regulators known to mediate transcriptional repression, including those listed in Table 3. Each shRNA was packaged into lentivirus particles and transduced into undifferentiated induced pluripotent stem cells (iPSCs) derived from fibroblasts from an FA patient (Ku et al. 2010, *Cell Stem Cell* 7:631-637), i.e., the FA iPSC line GM23404 (obtained from the Coriell Institute for Medical Research) derived from an FA patient, GM03816, who has alleles of −330 and 380 GAA-TTC repeats and exhibits spinal-cerebral degeneration and cardiomyopathy. These FA iPSCs harbor a repressed TRE-FXN gene, and therefore serve as a useful model system for studying disease mechanisms and for drug screening approaches. Twenty days post-transfection, mRNA was prepared and FXN expression analyzed by quantitative RT-PCR (qRT-PCR). A candidate was considered to be positive if at least two unrelated shRNAs directed against the same target resulted in: (1) a statistically significant increase in FXN transcription compared to that obtained with a control non-silencing (NS) shRNA, and (2) decreased mRNA levels of the target gene. A representative subset of the results obtained in the complete screen of the 162 shRNAs is shown in FIG. 1A, which enabled us to identify 10 epigenetic repressors of the TRE-FXN gene: DNMT3A, DNMT3B, EZH2, SETDB1, EHMT2/G9a, RING1B/RNF2, KDM5A, HDAC2, HDAC5, and SIRT7 (Table 4). For convenience we refer to these factors as FXN Repressing Factors (FXN-RFs). The immunoblot results of FIG. 1B show that knockdown of each FXN-RF also increased frataxin protein to levels comparable to that observed in an iPSC line derived from a normal individual (BJ1-iPS4 cells (Sheridan et al., PLoS One 6(10): e26203); hereafter called normal iPSCs).

TABLE 4

List of 10 FXN-RFs and their epigenetic roles

| FXN-RF | Role |
| --- | --- |
| DNMT3A | DNA methyltransferase |
| DNMT3B | DNA methyltransferase |
| EZH2 | PRC2 (H2K27 methyltransferase) |
| SETDB1 | H3K9 methyltransferase |
| EHMT2/G9a | H3K9 methyltransferase |
| RING1B/RNF2 | PRC1 (H2A ubiquitin ligase) |
| KDM5A | H3K4 demethylase |
| HDAC2 | Histone deacetylase |
| HDAC5 | Histone deacetylase |
| SIRT7 | Sirtuin |

Figure 1C:
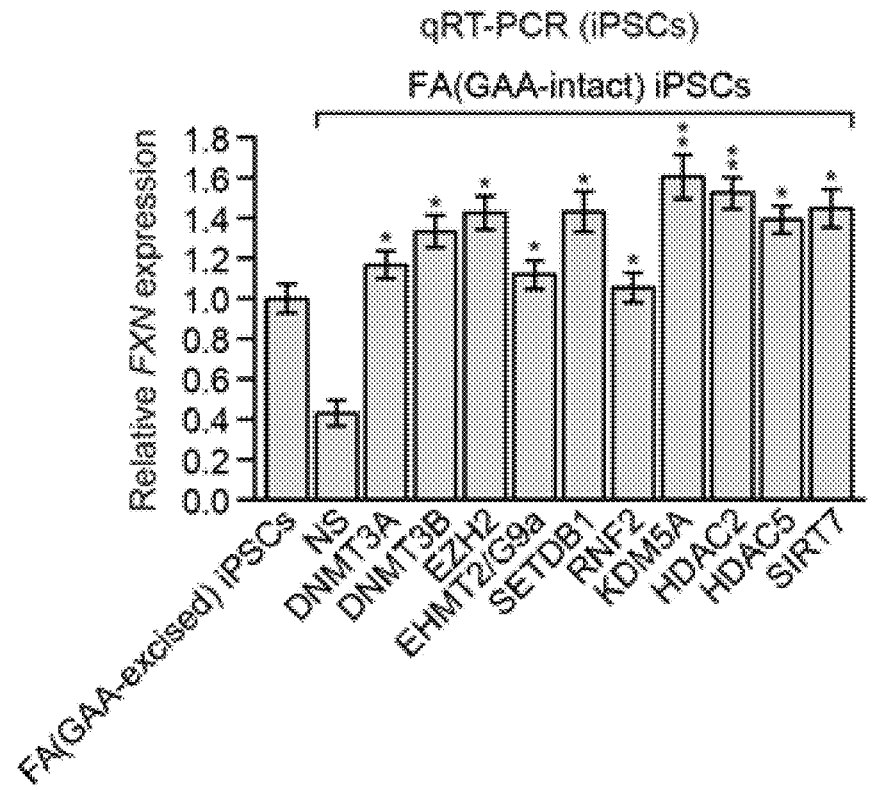

To confirm these results, an isogenic pair of FA IPSC lines was obtained (from Marek Napierala, University of Alabama School of Medicine) in which the GAA•TTC repeat is either intact (GAA-intact) or has been deleted on one allele (GAA-excised) (Li et al. 2015, Mol Ther 23:1055). The cell lines were derived from an FA patient, FRDA68, who has alleles of −1400 and 560 GAA•TTC repeats; the GAA-excised derivative contains only the allele with 560 repeats. This pair of isogenic FA cell lines is a powerful experimental tool that recapitulates the difference in FXN transcription between asymptomatic carriers and FA patients and controls for individual differences in gene expression. FIG. 1C shows that knockdown of each FXN-RF in FA(GAA-intact) iPSCs upregulated TRE-FXN transcription to levels comparable to that observed in FA(GAA-excised) iPSCs.

Figure 1D:
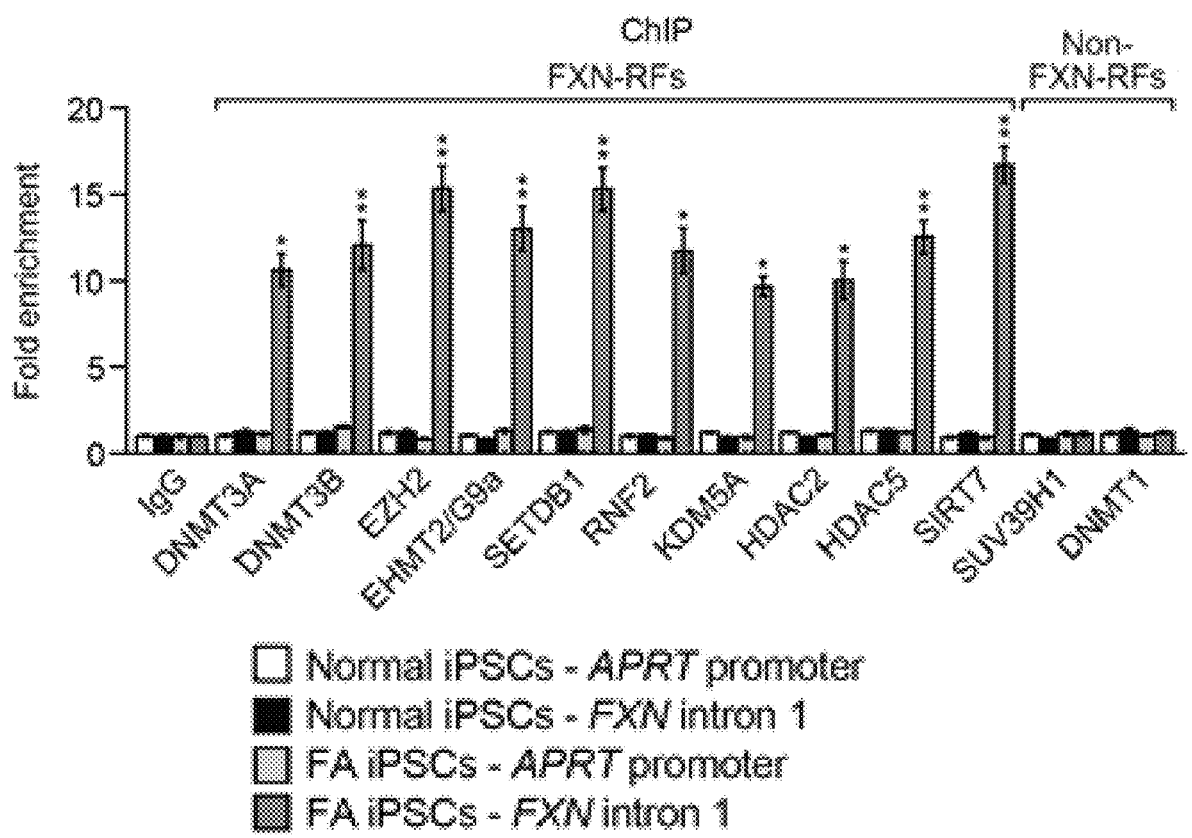
FIGS. 1D-1G show that FXN-RFs associate with the first intron of the TRE-FXN gene and are sequentially recruited in an ordered pathway.

Epigenetic regulators are typically associated with the promoters and/or genes upon which they act. To determine whether the 10 FXN-RFs are associated with the TRE-FXN gene chromatin immunoprecipitation (ChIP) experiments were performed. FIG. 1D shows that in FA(GM23404) iPSCs all 10 FXN-RFs are enriched within the first intron of the TRE-FXN gene, which is the site of the GAA•TTC repeats, and, as expected, not on the first intron of the FXN gene in normal iPSCs or on a representative transcriptionally active control promoter (APRT). Furthermore, SUV39H1 or DNMT1, which are not involved in repression of TRE-FXN (see FIG. 1A), were not enriched on the first intron of the TRE-FXN gene.

Figure 1E:
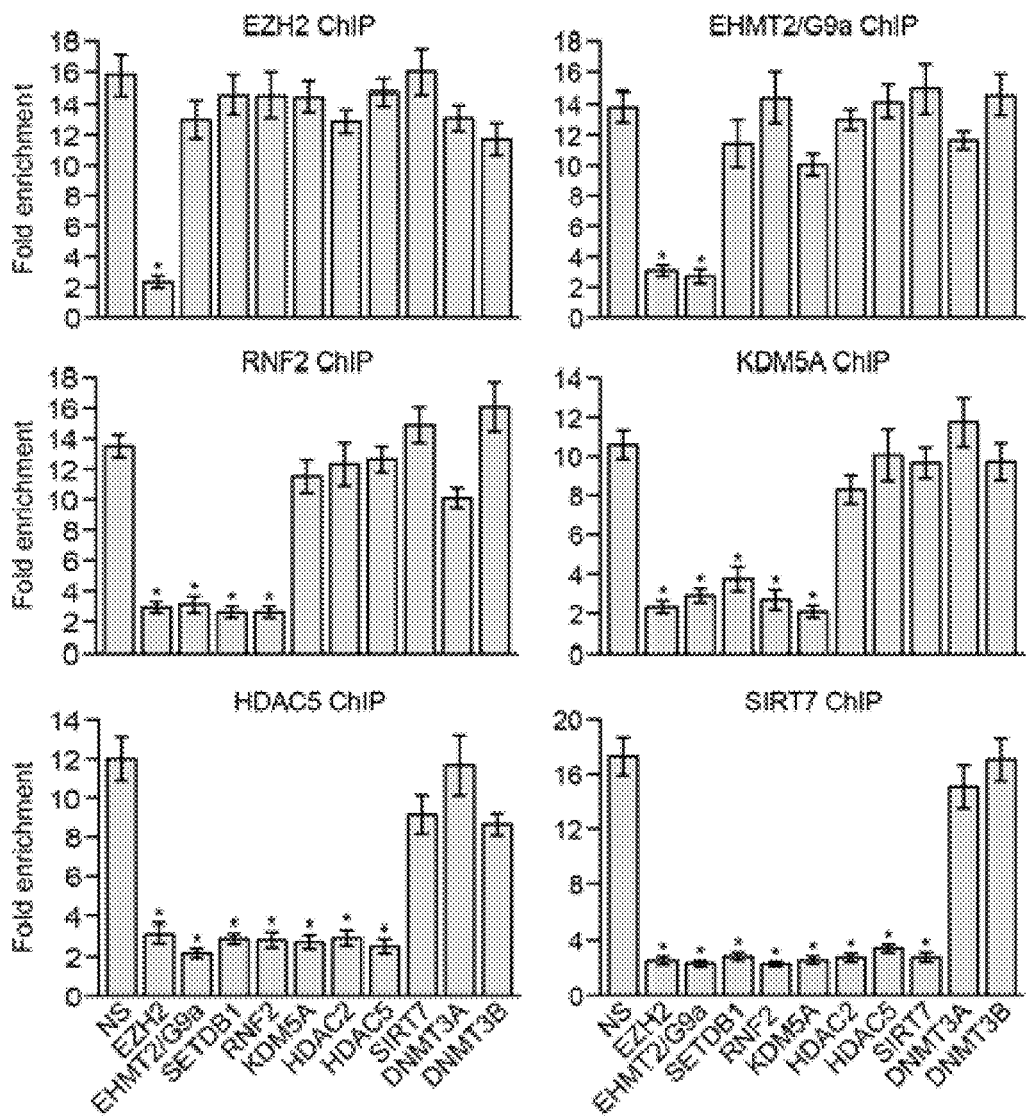
Figure 1F:
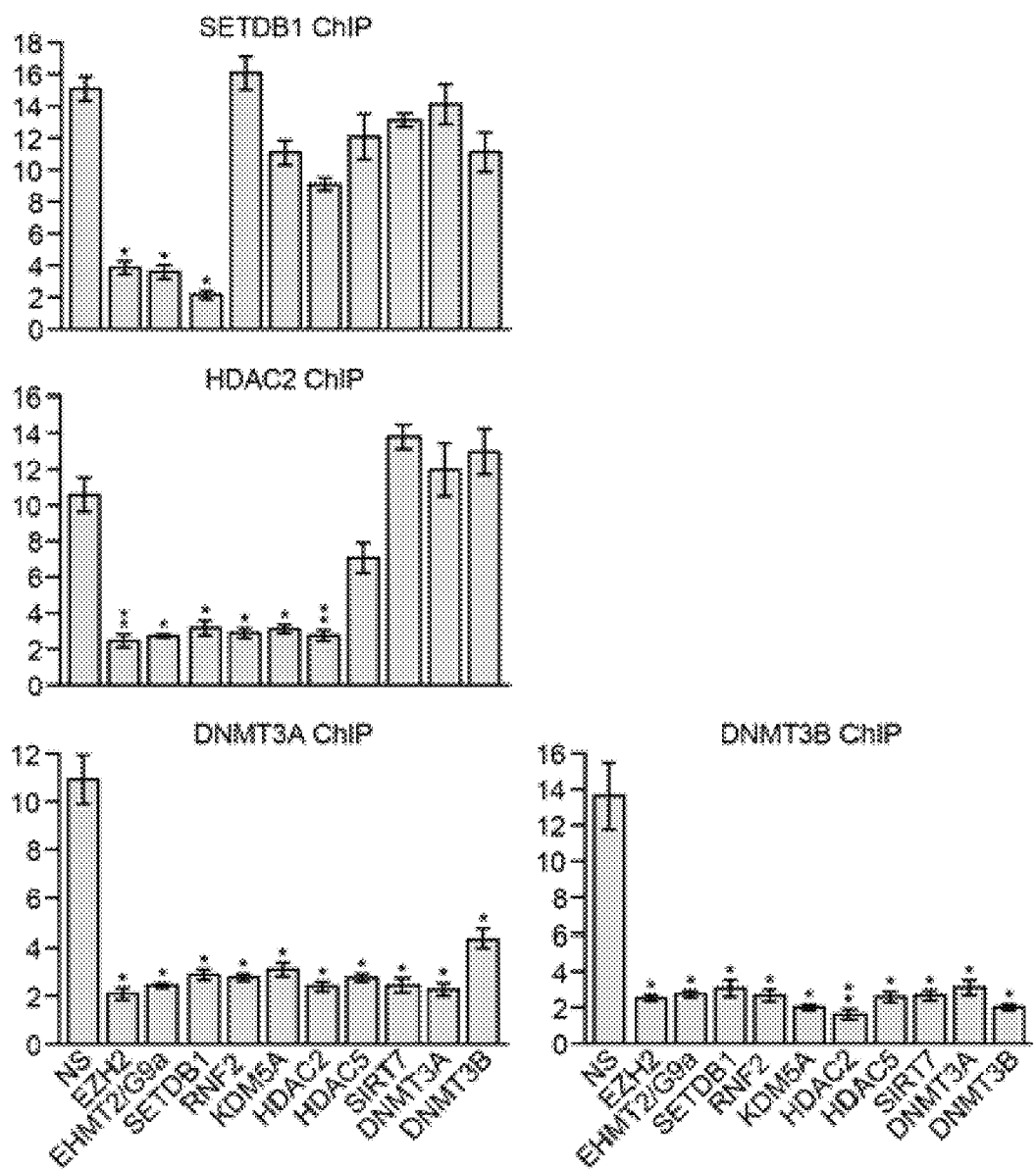
Figure 1G:
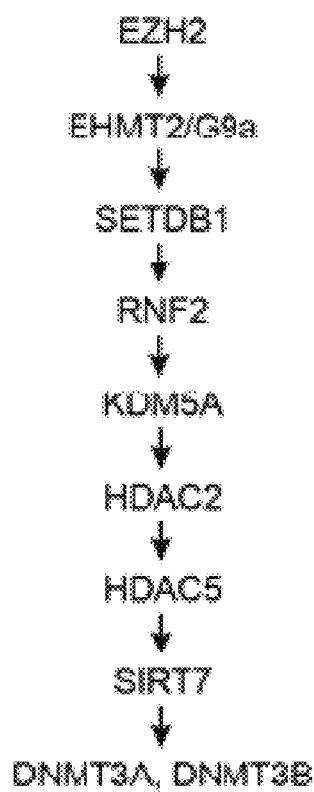

As previously shown, factors involved in epigenetic silencing of a tumor suppressor gene in cancer cells are recruited to the promoter in an ordered pathway resulting from sequential recruitment by other, previously-bound epigenetic regulators (Wajapeyee et al., (2013) Genes Dev 27(20): 2221-6). This conclusion was based on RNAi-based epistasis analysis, in which each epigenetic repressor is systematically knocked down and the effect on binding of all epigenetic repressors is determined in a ChIP assay. To determine if epigenetic repression of TRE-FXN occurs through a similar mechanism of ordered FXN-RF recruitment, RNAi-based epistasis analysis was performed for the 10 FXN-RFs. FIGS. 1E-F shows that binding of EZH2 did not require any of the other FXN-RFs, allowing us to place it first in the recruitment pathway. By contrast, binding of DNMT3A (FIGS. 1E-F) and DNMT3B were dependent upon all of the FXN-RFs, allowing them to be placed last in the pathway. The other seven FXN-RFs analyzed showed a dependence on other FXN-RFs that was intermediate to that of EZH2 and DNMT3A/3B (due to space limitations only a representative intermediary FXN-RF, KDM5A, is shown in FIGS. 1E-F). Collectively, this epistasis analysis enabled us to construct an ordered pathway of FXN-RF recruitment to the first intron of the TRE-FXN gene that is summarized in FIG. 1G.

Figure 1H:
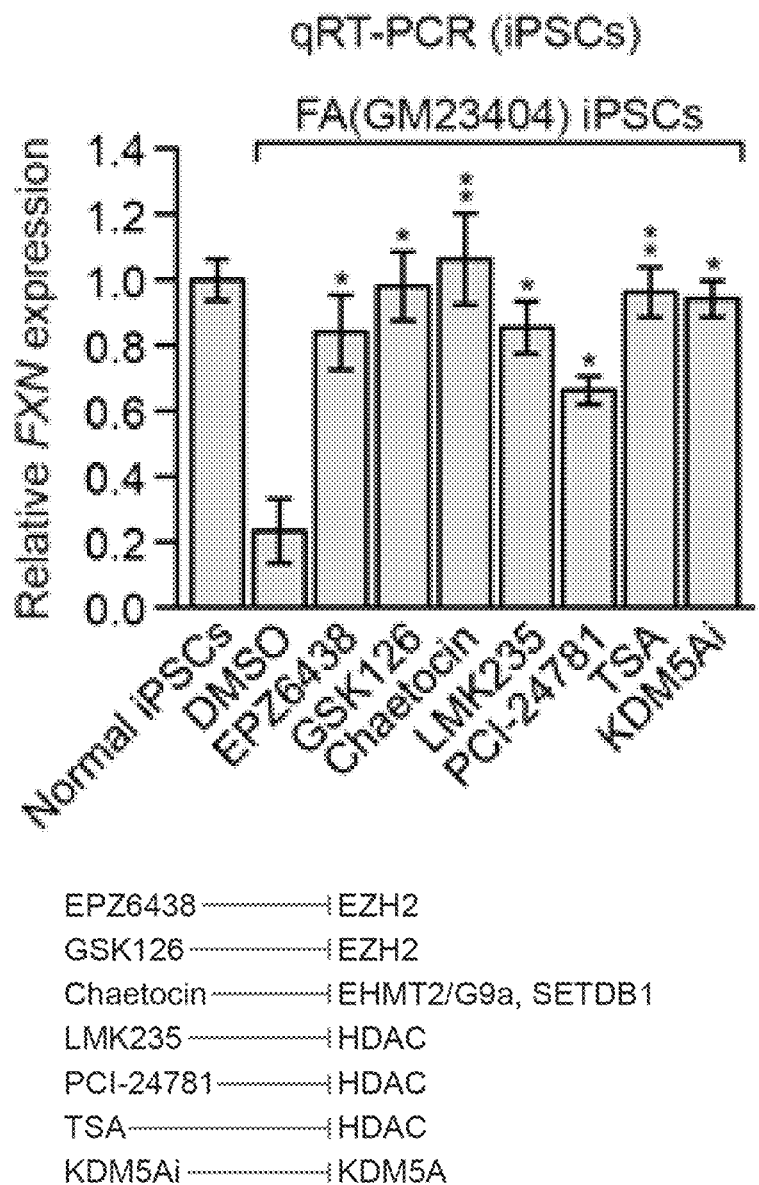
FIGS. 1H-1K show transcriptional upregulation of TRE-FXN by small molecule FXN-RF inhibitors.
Figure 1I:
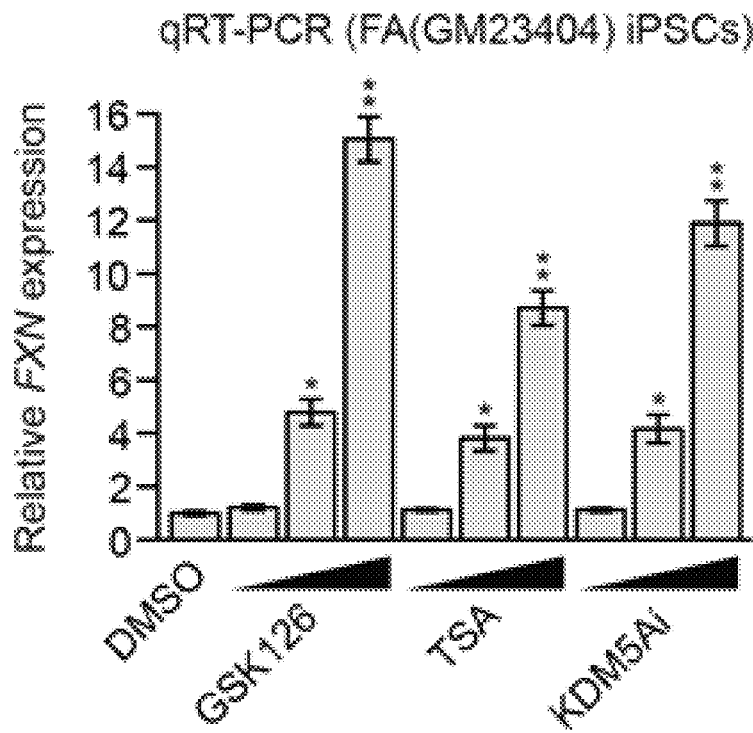
Figure 1J:
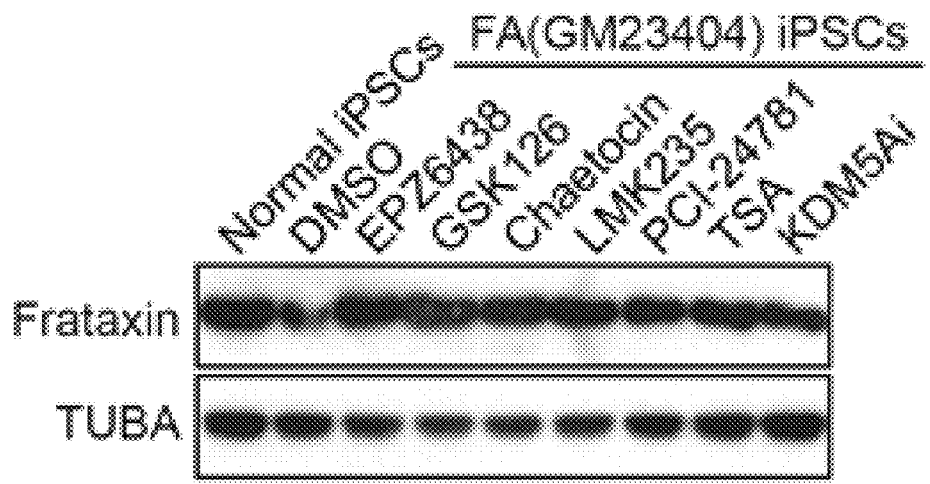
Figure 1K:
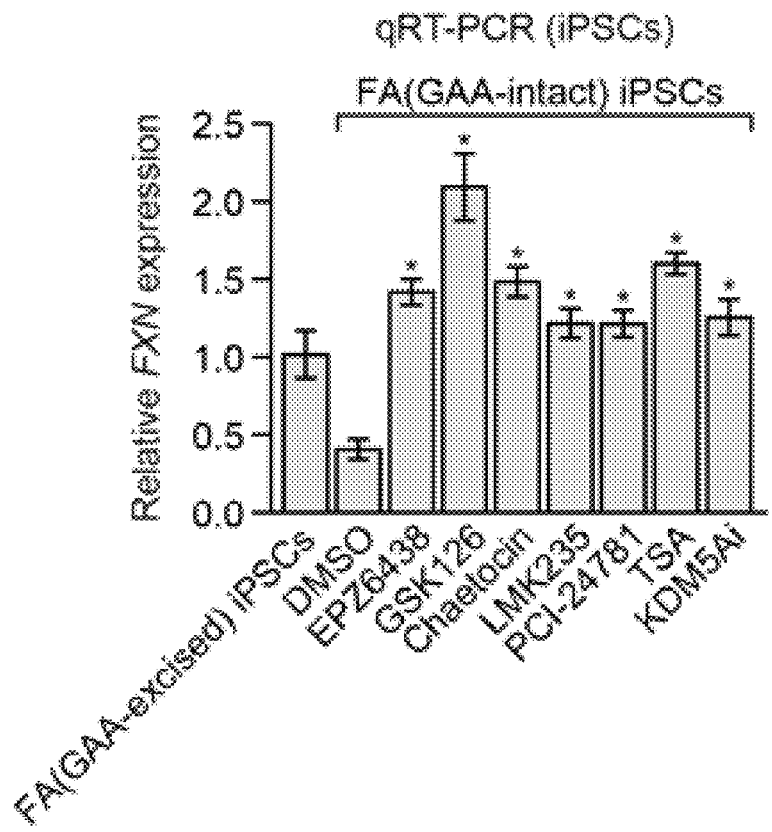

For several of the FXN-RFs, small molecule inhibitors are available, and the next experiments tested whether small molecule inhibitors, like RNAi knockdown, could increase transcription of the TRE-FXN gene. To date, seven compounds have been tested: two EZH2 inhibitors (EPZ6438 and GSK126), the H3K9 methyltransferase inhibitor chaetocin (which targets SETDB1 and EHMT2/G9a), three HDAC inhibitors (LMK235, PCI-24781 and trichostatin A (TSA)), and a KDMSA inhibitor (KDM5Ai). The qRT-PCR results of FIG. 1H show that treatment of FA(GM23404) iPSCs with any one of the small molecule FXN-RF inhibitors upregulated TRE-FXN transcription, resulting in FXN mRNA levels comparable to that observed in normal iPSCs. Upregulation of TRE-FXN transcription by three representative small molecule FXN-RF inhibitors was, as expected, dose dependent (FIG. 10. The immunoblot of FIG. 1J shows that all small molecule FXN-RF inhibitors tested also increased frataxin to levels comparable to that observed in normal iPSCs. Analysis in a second FA iPSC line confirmed that all of the small molecule FXN-RF inhibitors tested upregulated TRE-FXN transcription in FA(GAA-intact) iPSCs, resulting in FXN mRNA levels comparable to, and in some cases even greater than, that observed in FA(GAA-excised) iPSCs (FIG. 1K).

Figure 2A:
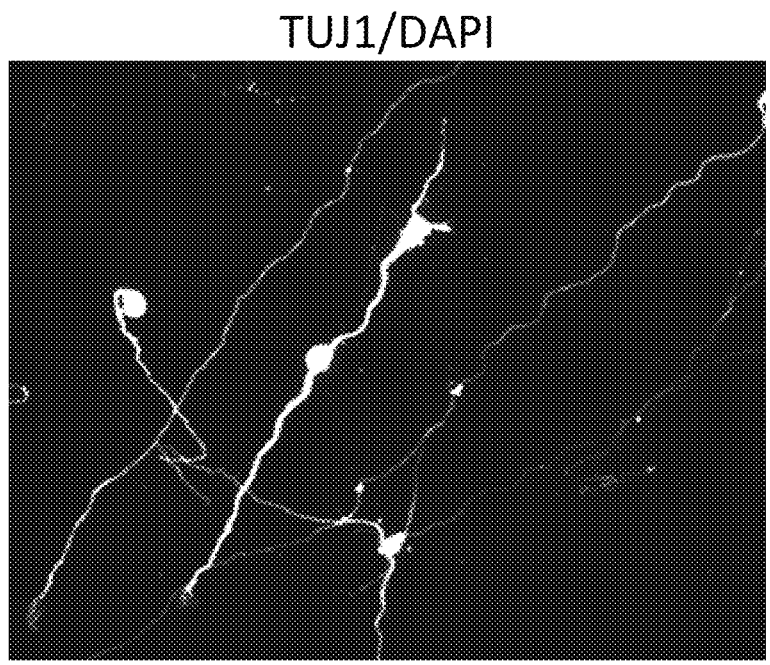
FIGS. 2A-2F show that FXN-RFs also mediated epigenetic repression of the TRE-FXN gene in post-mitotic FA neurons.
Figure 2B:
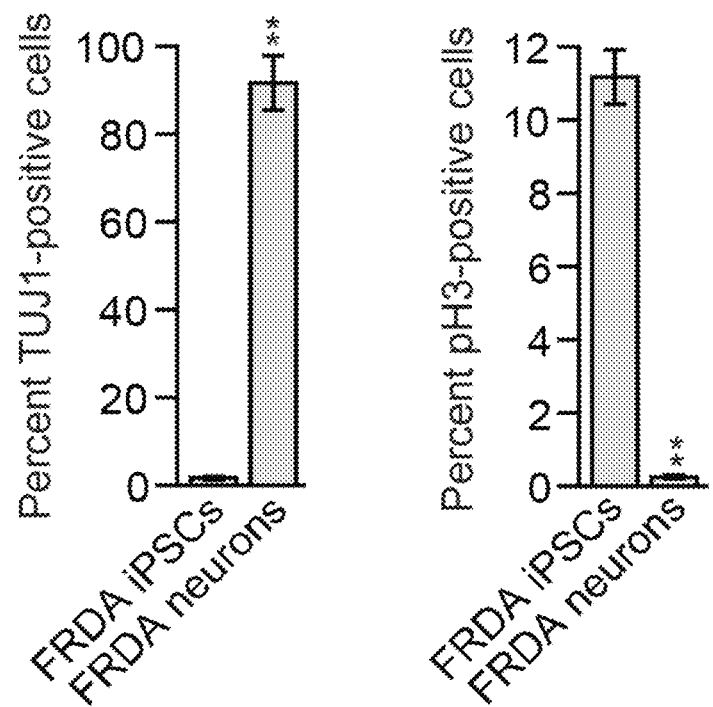
Figure 2C:
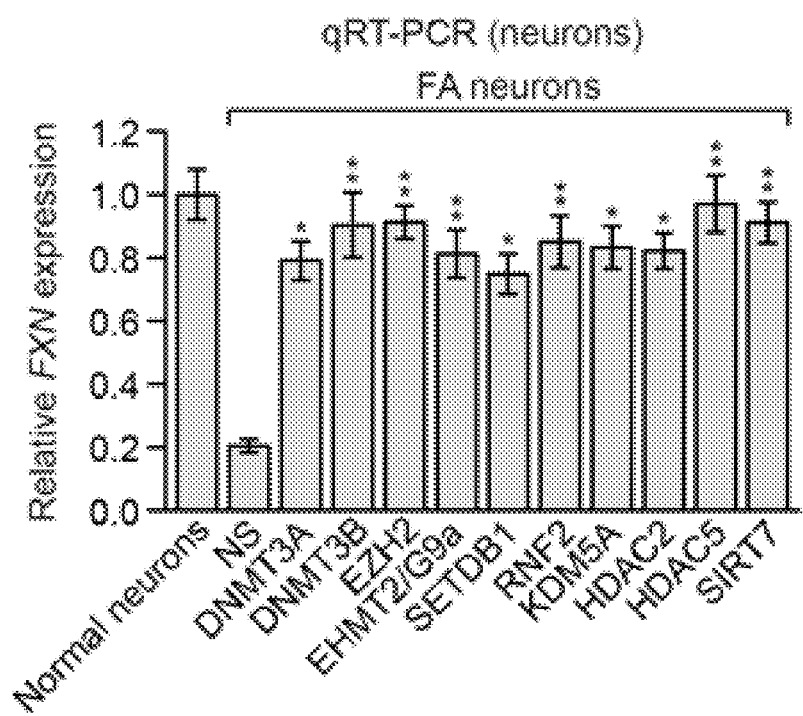
Figure 2D:
Figure 2E:
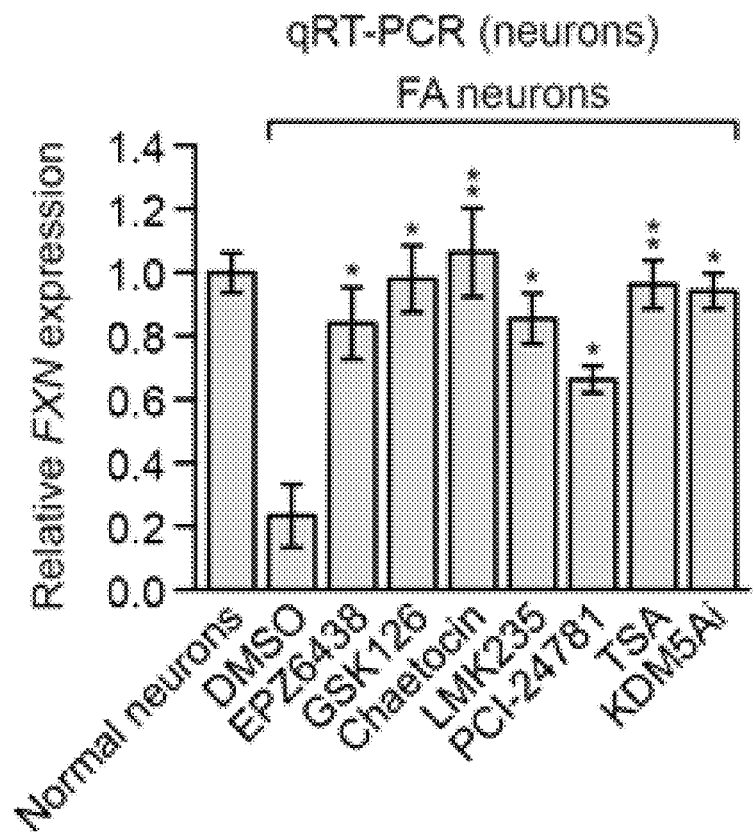
Figure 2F:
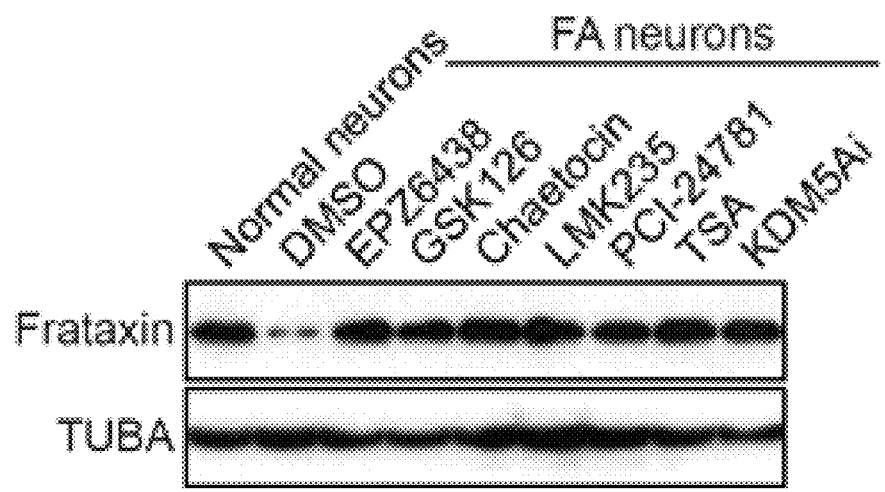

Example 2. Inhibiting FXN-RFs Leads to De-Repression of FXN Expression in FA Post-Mitotic Neurons The next experiments asked whether inhibition of the same set of FXN-RFs would also upregulate transcription of the TRE-FXN gene in post-mitotic neurons, which is the cell type most relevant to FA. To derive post-mitotic FA neurons, FA(GM23404) iPSCs were stably transduced with lentiviral vectors over-expressing Neurogenin-1 and Neurogenin-2 to drive neuronal differentiation, according to published methods (Busskamp et al. 2014, Mol Syst Biol 10:760); for convenience, these cells are referred to herein as FA neurons. Neuronal differentiation was assessed and confirmed by staining with the neuronal marker TUJ1 (FIG. 2A). As expected, the FA neurons were post-mitotic as evidenced by the lack of the mitotic marker phosphorylated histone H3 (FIG. 2B). Treatment of FA neurons with an shRNA targeting any one of the 10 FXN-RFs upregulated TRE-FXN transcription (FIG. 2C) and increased frataxin (FIG. 2D) to levels comparable to that of normal neurons. Likewise, treatment of FA neurons with small molecule FXN-RF inhibitors also upregulated TRE-FXN transcription (FIG. 2E) and increased frataxin (FIG. 2F) to levels comparable to that of normal neurons.

Figure 3A:
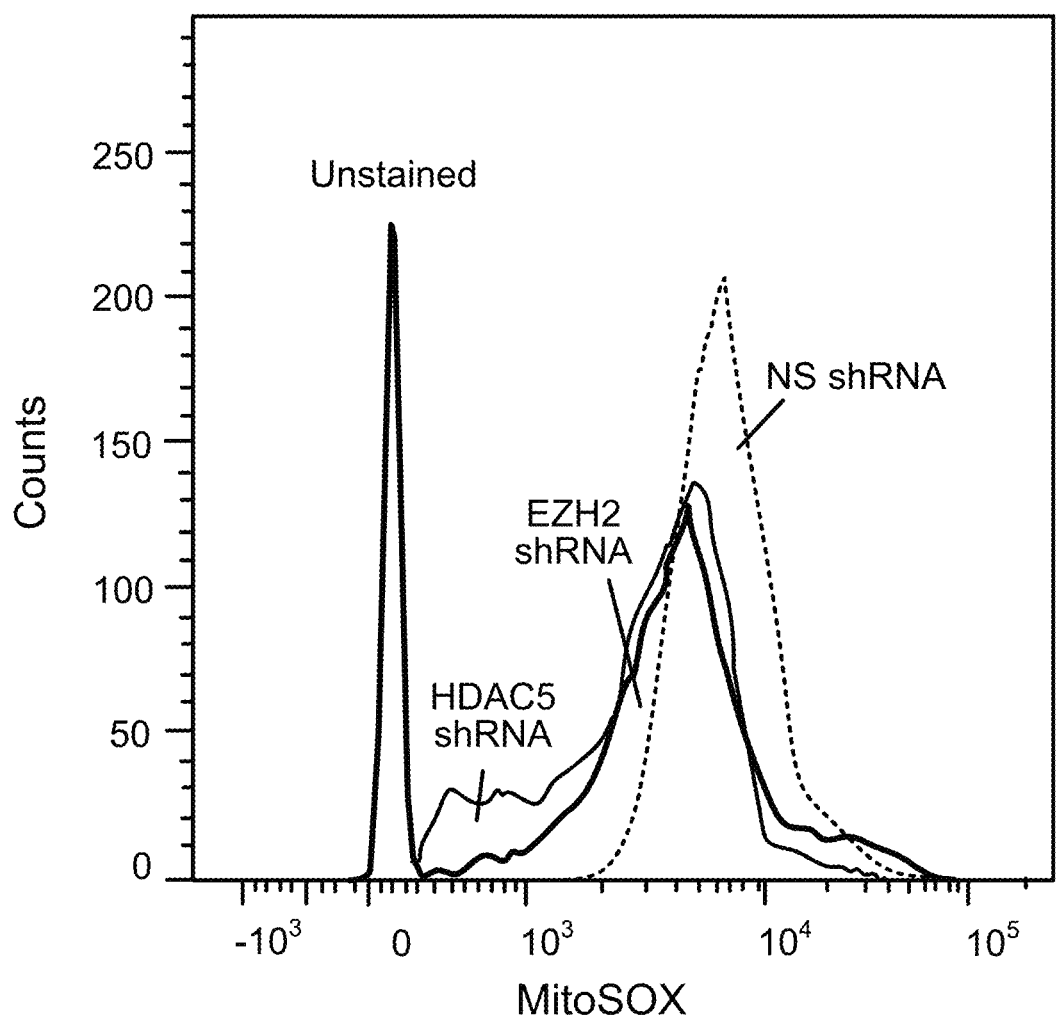
FIGS. 3A-3C show inhibition of FXN-RFs can ameliorate characteristic mitochondrial defects of FA post-mitotic neurons.
Figure 3B:
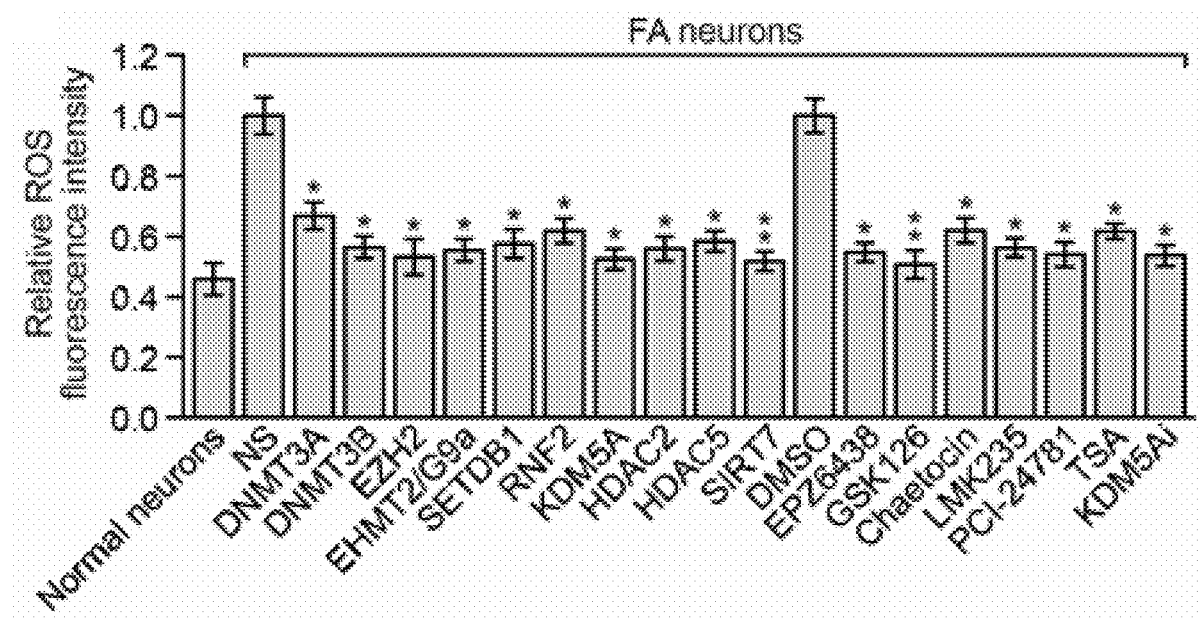
Figure 3C:
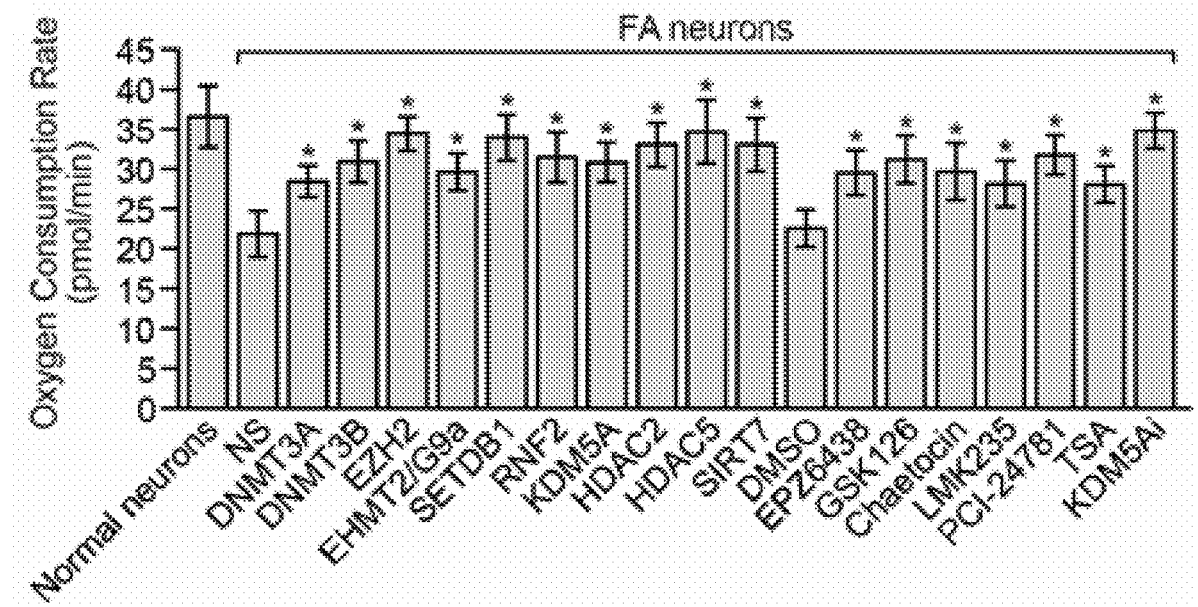

It was next determined whether shRNA-mediated inhibition of FXN-RFs could ameliorate two of the characteristic mitochondrial defects of FA neurons: (1) increased levels of reactive oxygen species (ROS), and (2) decreased oxygen consumption. To assay for mitochondrial dysfunction, FA neurons an FXN-RF shRNA or treated with a small molecule FXN-RF inhibitor were stained with MitoSOX, (an indicator of mitochondrial superoxide levels, or ROS-generating mitochondria) followed by FACS analysis. FIG. 3A shows that FA neurons expressing an NS shRNA accumulated increased mitochondrial ROS production compared to EZH2- or HDAC5-knockdown FA neurons. FIG. 3B shows that FA neurons had increased levels of mitochondrial ROS production compared to normal neurons (Codazzi et al., (2016) *Hum Mol Genet* 25(22): 4847-485). Notably, inhibition of FXN-RFs in FA neurons restored mitochondrial ROS production to levels comparable to that observed in normal neurons. In the second set of experiments, mitochondrial oxygen consumption, which is related to ATP production, was measured using an Agilent Seahorse XF Analyzer (Divakaruni et al., (2014) *Methods Enzymol* 547:309-54). FIG. 3C shows that oxygen consumption in FA neurons was ~60% of the level observed in normal neurons. Notably, inhibition of FXN-RFs in FA neurons restored oxygen consumption to levels comparable to that observed in normal neurons. Collectively, these preliminary results provide important proof-of-concept that inhibition of FXN-RFs can ameliorate the mitochondrial defects of FA post-mitotic neurons.

Mitochondrial dysfunction results in reduced levels of several mitochondrial Fe-S proteins, such as aconitase 2 (ACO2), iron-sulfur cluster assembly enzyme (ISCU) and NADH:ubiquinone oxidoreductase core subunit S3 (NDUFS3), and lipoic acid-containing proteins, such as pyruvate dehydrogenase (PDH) and 2-oxoglutarate dehydrogenase (OGDH), as well as elevated levels of mitochondria superoxide dismutase (SOD2) (Urrutia et al., (2014) *Front Pharmacol* 5:38). Immunoblot analysis is performed using methods known in the art to determine whether treatment with an FXN-RF shRNA or a small molecule FXN-RF inhibitor restores the normal levels of these mitochondrial proteins in FA neurons.

Figure 4A:
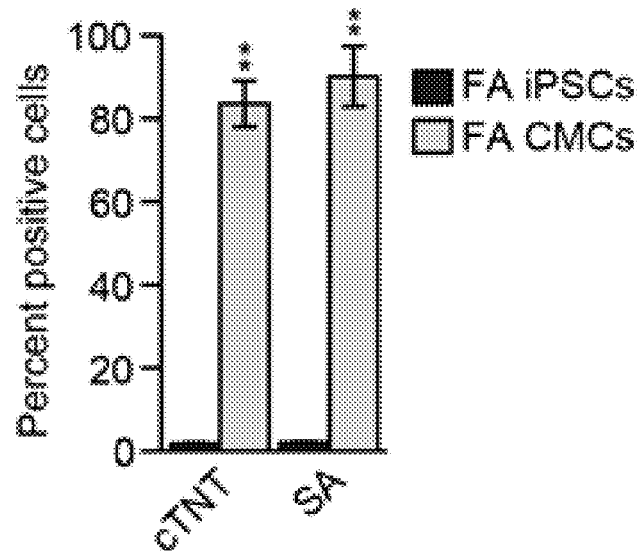
FIGS. 4A-4E show that FXN-RFs also mediate epigenetic repression of the TRE-FXN gene in FA cardiomyocytes.
Figure 4B:
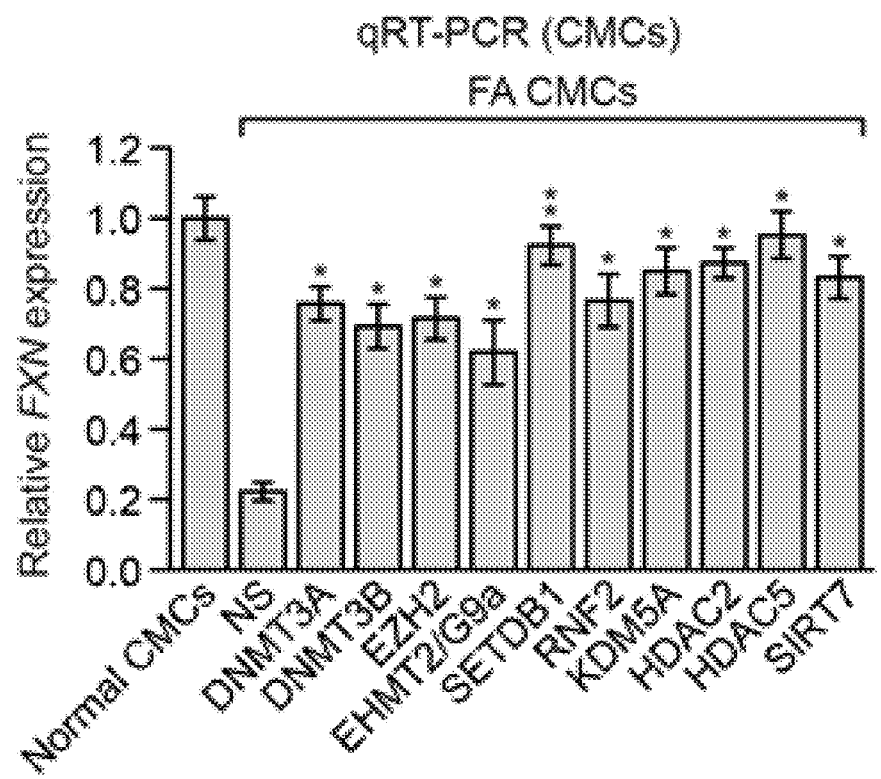
Figure 4C:
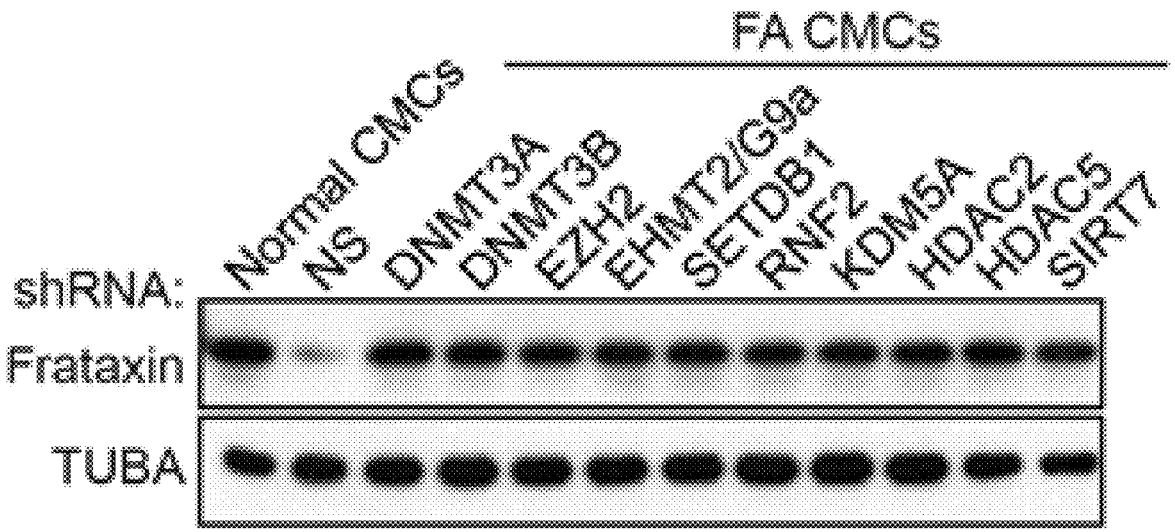
Figure 4D:
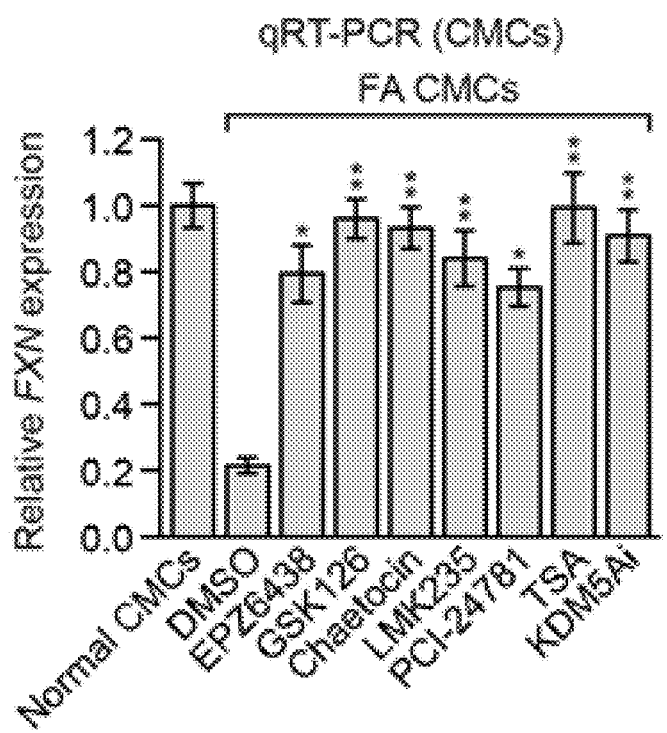
Figure 4E:
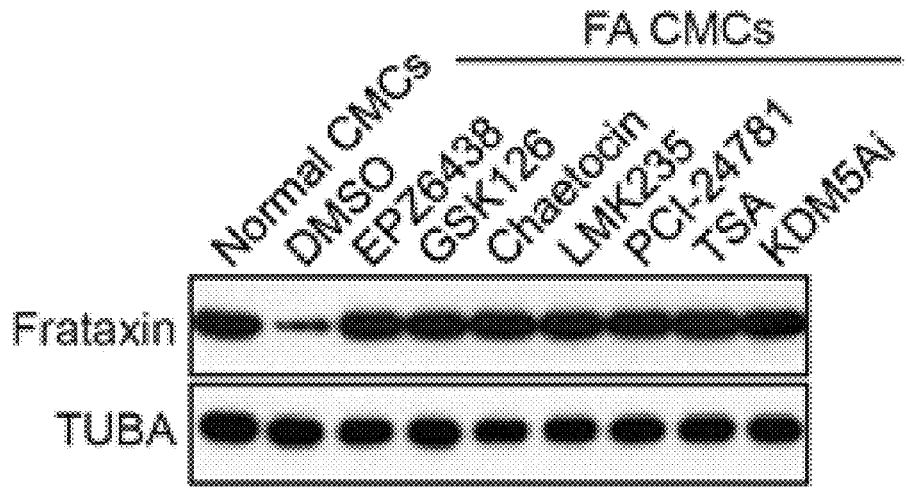

Example 3. Inhibiting FXN-RFs Leads to De-Repression of FXN Expression in FA Cardiomyocytes The next experiments were performed to determine whether inhibition of the same set of FXN-RFs would also upregulate transcription of the TRE-FXN gene in cardiomyocytes. To derive FA cardiomyocytes, a published method was used in which iPSCs are sequentially cultured in chemically defined media (Burridge et al., (2011) *PLoS One* 6(4): e18293). In brief, FA(GM23404) iPSCs were cultured for two days with chemically defined medium ("CDM3", consisting of RPMI 1640 medium, albumin and ascorbic acid) supplemented with the GSK3β inhibitor and Wnt signaling activator CHIR99021, then cultured for two days with CDM3 supplemented with the Wnt inhibitor Wnt-059, and finally cultured with CDM3 alone. The colonies were dissociated and re-seeded to derive single cardiomyocytes. Cardiomyocyte differentiation occurred within 10-14 days and was assessed and confirmed by staining with the cardiomyocyte-specific markers cardiac troponin T and sarcomeric actinin (Dell'Era et al., (2015) *World J Stem Cells* 7(2): 329-42) (FIG. 4A). Treatment of FA cardiomyocytes with an shRNA targeting any one of the 10 FXN-RFs upregulated TRE-FXN transcription (FIG. 4B) and increased fraxatin (FIG. 4C) to levels comparable to that of normal cardiomyocytes. Similarly, treatment of FA cardiomyocytes with small molecule FXN-RF inhibitors also upregulated TRE-FXN transcription (FIG. 4D) and increased frataxin (FIG. 4E) to levels comparable to that of normal cardiomyocytes.

Figure 5A:
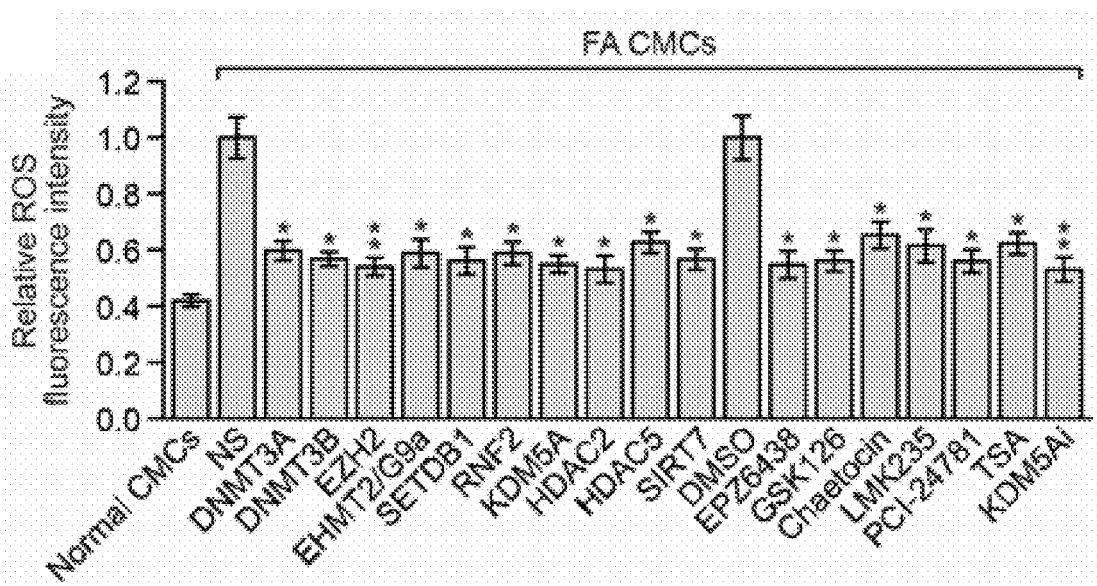
FIGS. 5A-5B show that inhibition of FXN-RFs can ameliorate the characteristic mitochondrial defects of FA cardiomyocytes.
Figure 5B:
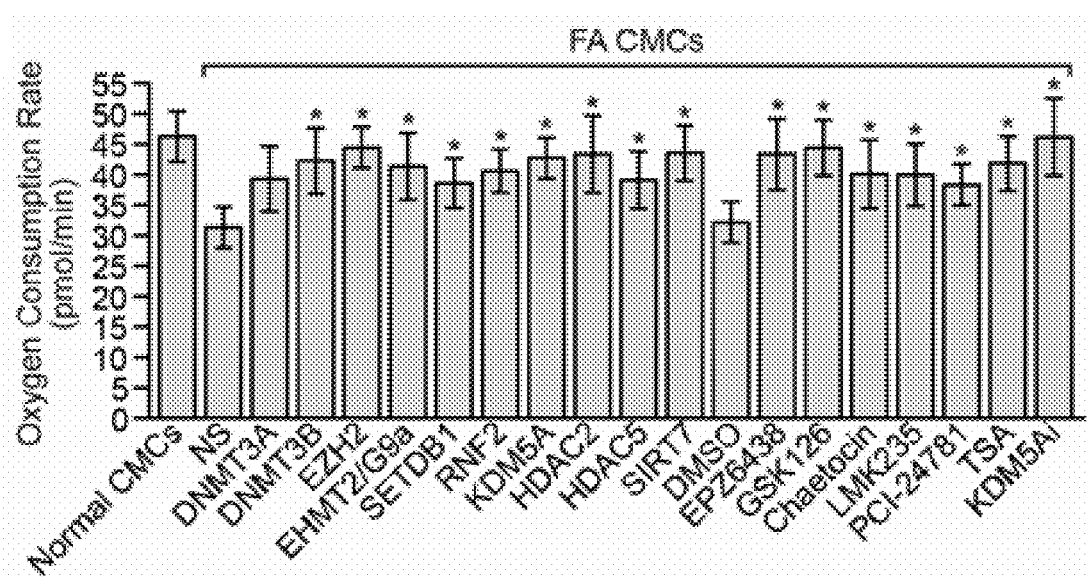

Further experiments were performed to determine whether inhibition of FXN-RFs by shRNAs or small molecule inhibitors could, as in FA neurons (see FIGS. 3A-C), ameliorate characteristic mitochondrial defects of FA cardiomyocytes. FIG. 5A shows, as expected, that FA cardiomyocytes had increased levels of mitochondrial ROS production compared to normal neurons [56]. Notably, inhibition of FXN-RFs in FA cardiomyocytes restored mitochondrial ROS production to levels comparable to that observed in normal cardiomyocytes. FIG. 5B shows that oxygen consumption in FA cardiomyocytes was ~68% of the level observed in normal neurons. Notably, inhibition FXN-RFs in FA neurons restored oxygen consumption to levels comparable to that observed in normal neurons. Collectively, these preliminary results provide important proof-of-concept that inhibition of FXN-RFs can ameliorate the mitochondrial defects of FA cardiomyocytes.

Immunoblot analysis is also performed using methods known in the art to determine whether treatment with an FXN-RF shRNA or a small molecule FXN-RF inhibitor restores normal levels of mitochondrial proteins (e.g., ACO2, ISCU, NDUFS3, PDH, OGDH, SOD2) in FA cardiomyocytes.

Figure 6:
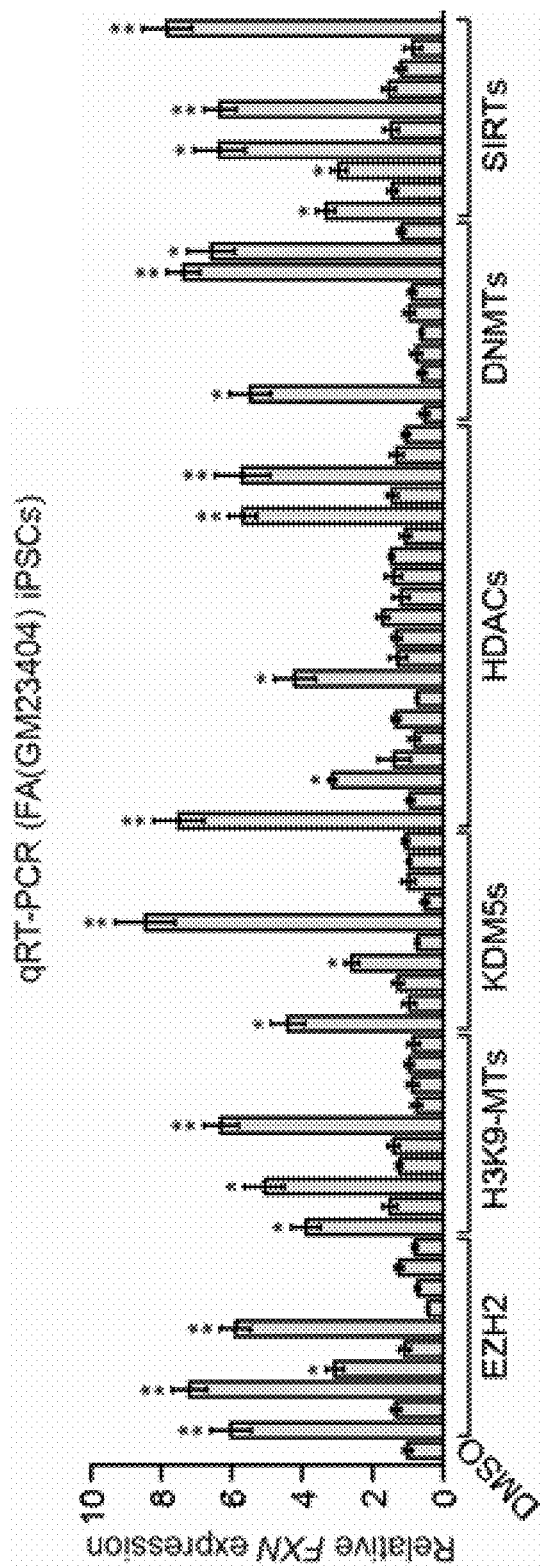
FIG. 6 shows identification of additional small molecule FXN-RF inhibitors from a small-scale pilot screen. qRT-PCR analysis monitoring FXN transcription in FA(GM23404) iPSCs treated with 70 small molecule compounds that are predicted be inhibitors of nine of the FXN-RFs. The results were normalized to that obtained with DMSO, which was set to 1. H3K9-MTs, H3K9 methyltransferases. Data are represented as mean±SD (n=3 technical replicates of a representative experiment (out of 3 independent experiments)). *P<0.05, **P<0.01.
Figure 7A:
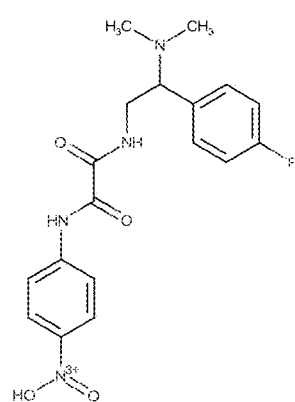
FIGS. 7A-7E show the structures of exemplary predicted inhibitors of EZH2 (F2880-2566; F5564-0146; F6235-0533; and F3407-3748, FIG. 7A); H3K9 methyltransferases (F2470-0099; F2880-1734; and F3222-4478, FIG. 7B); KDM5s, e.g., KDM5A or 5D (F3222-4242; F3358-0326; and F3385-1519, FIG. 7C); HDACs (F0307-0365; F3407-0197; F6196-0976; and F3095-0357, FIG. 7D); and DNMTs (F2578-0281; F3258-0176; and F3342-0131, FIG. 7E).
Figure 7A:
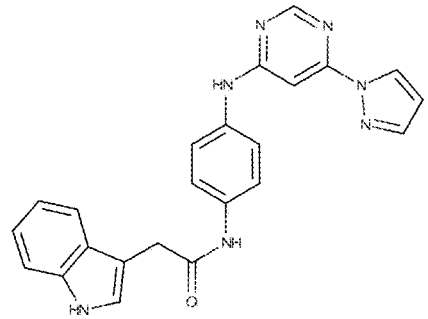
Figure 7A:
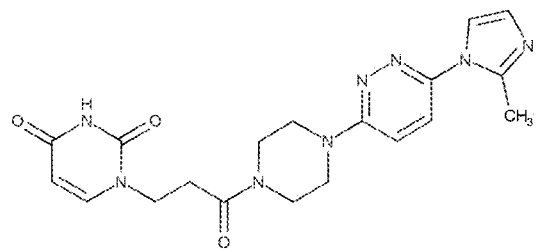
Figure 7A:
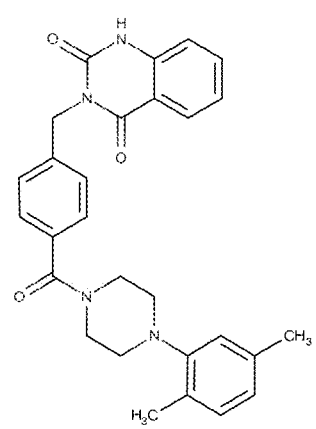
Figure 7B:
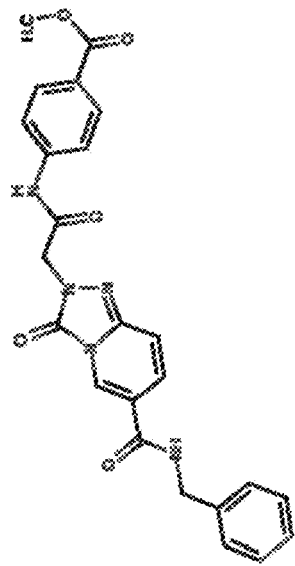
Figure 7B:
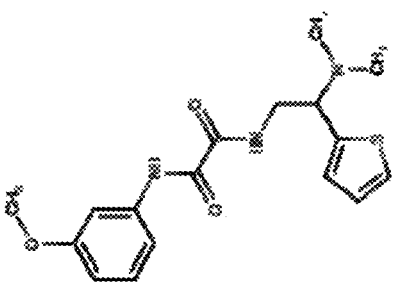
Figure 7B:
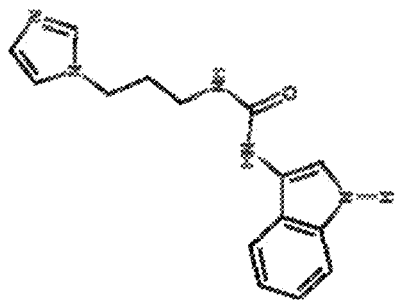
Figure 7C:
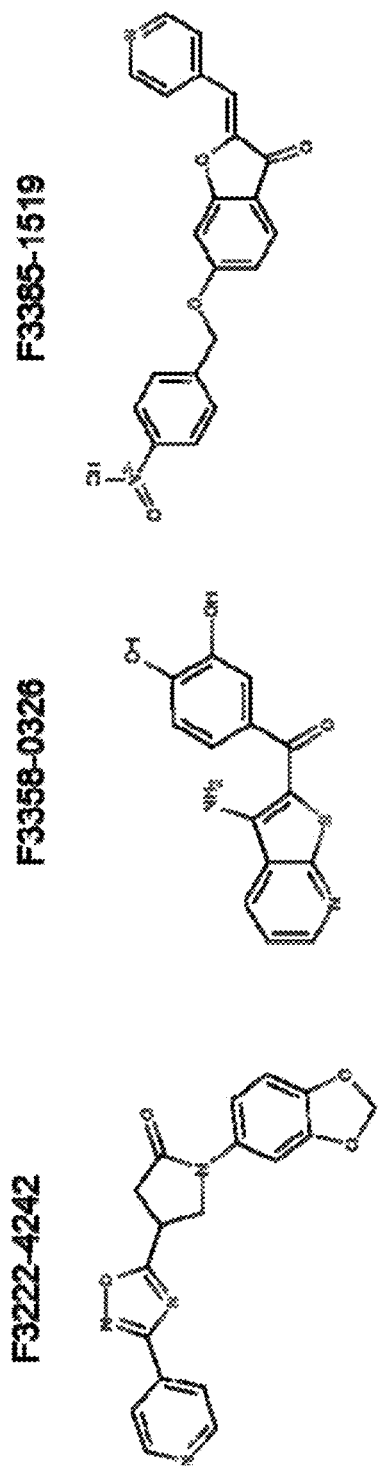
Figure 7D:
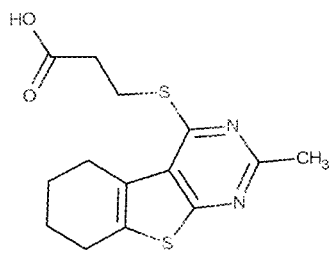
Figure 7D:
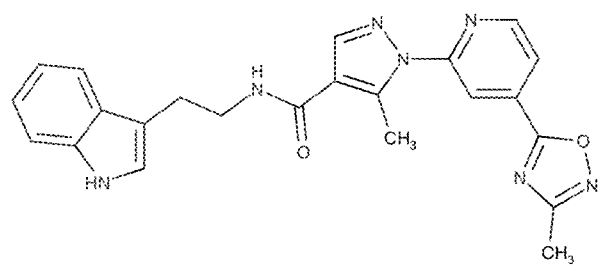
Figure 7D:
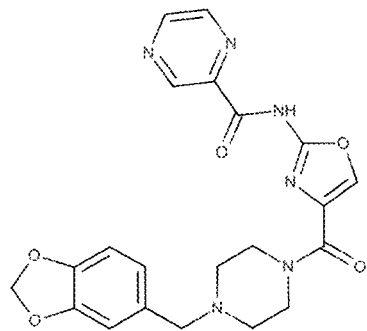
Figure 7D:
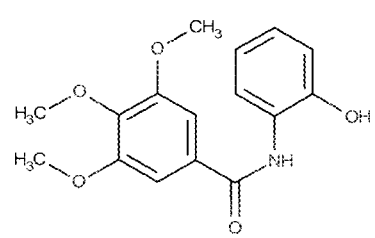
Figure 7E:
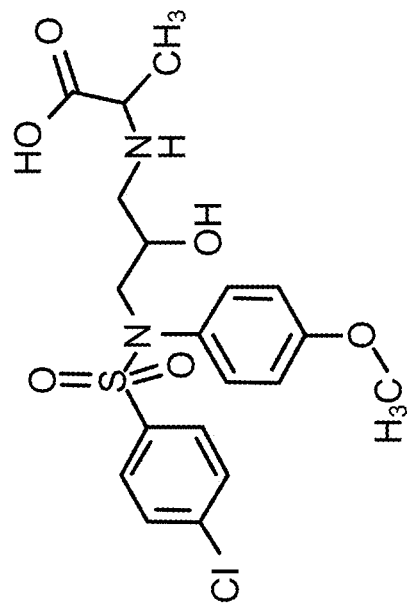
Figure 7E:
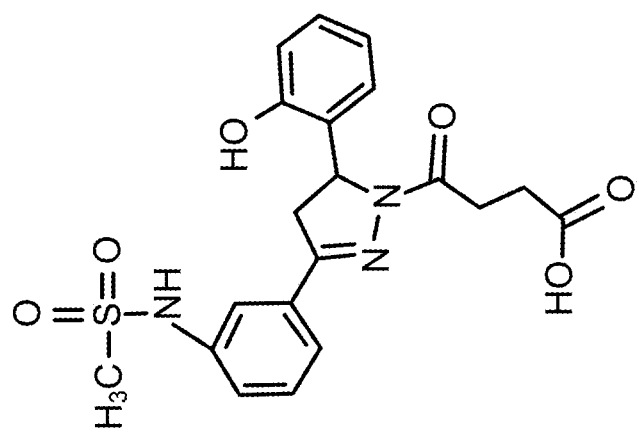
Figure 7E:
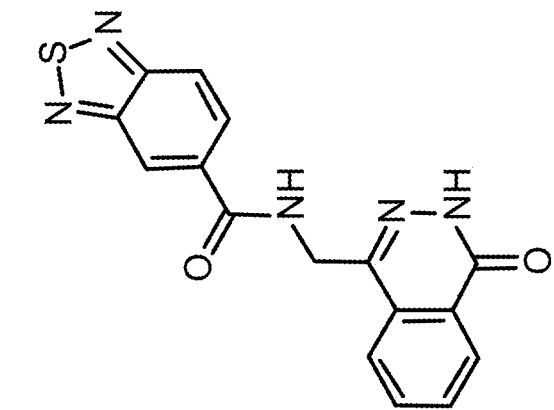
Figure 7F:
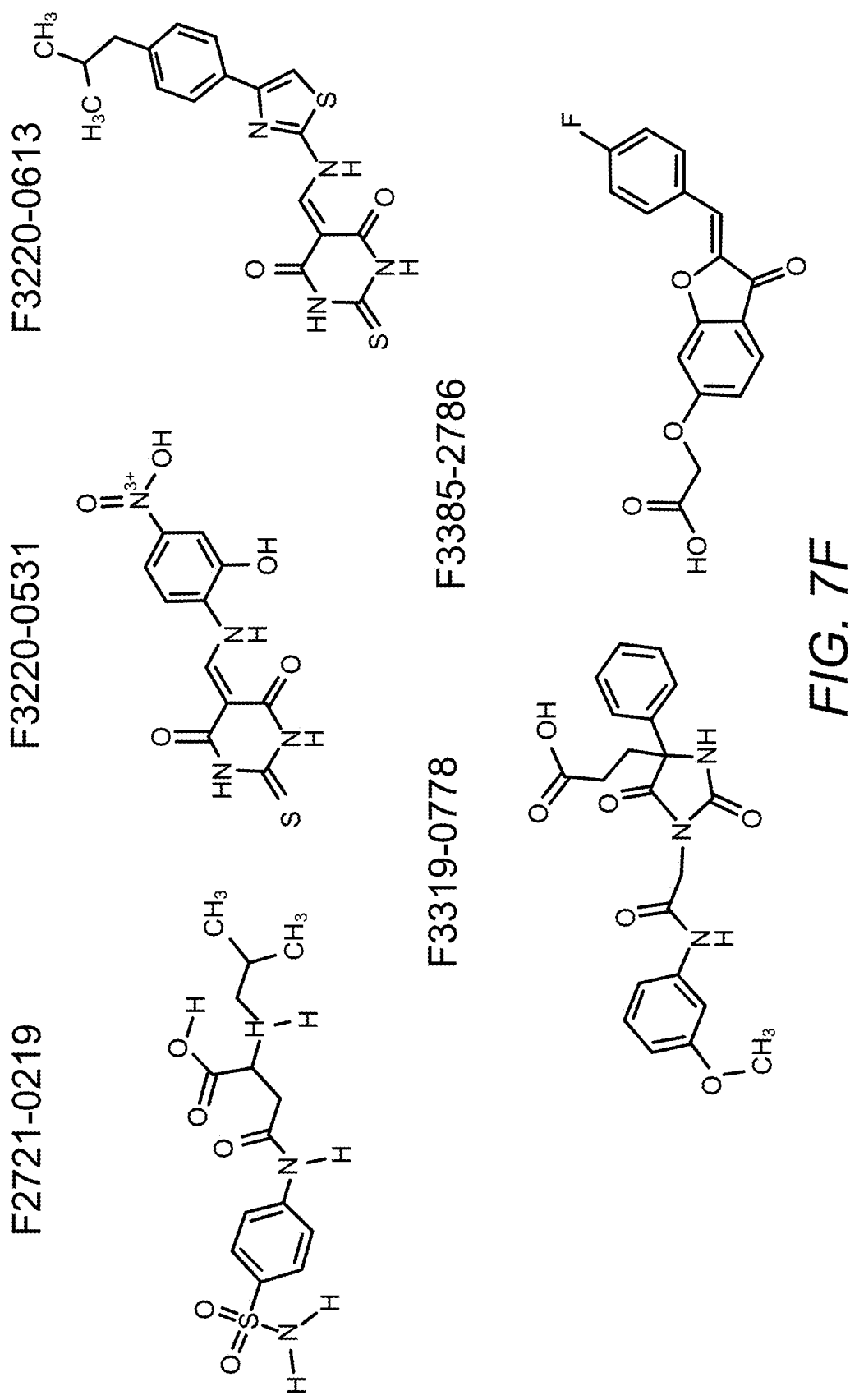
FIG. 7F shows the structure of exemplary predicted inhibitors of SIRTs, e.g., SIRT5 or SIRT7, including F2721-0219; F3220-0531; F3220-0613; F3319-0778; and F3385-2786.

Example 4. Identification of Additional Small Molecule Inhibitors of FXN-RFs One of the major objectives in identifying FXN-RFs is to ultimately obtain small molecule FXN-RF inhibitors. As a complementary approach to the shRNA screens for identifying new FXN-RFs, 70 small molecule compounds from the Epigenetics Targeted Library from Life Chemicals were screened. These compounds were chosen based on their predicted ability (based on a virtual docking and similarity search) to inhibit various classes of negative epigenetic regulators. The results, shown in FIG. 6, identified 23 compounds that upregulated transcription of the TRE-FXN gene. The structures of these compounds are shown in FIGS. 7A-F.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject having Friedreich ataxia (FA), the method comprising administering to the subject a therapeutically effective amount of a small molecule inhibitor of KDM5A in an amount sufficient to increase expression of frataxin protein,
    wherein the small molecule inhibitor of KDM5A is selected from the group consisting of: KDM5Ai, F3222-4242, F3358-0326, 2,4-PDCA, and JIB04.

2. The method of claim 1, wherein the small molecule inhibitor of KDM5A is KDM5Ai.

3. The method of claim 1, wherein the small molecule inhibitor of KDM5A is F3222-4242.

4. The method of claim 1, wherein the small molecule inhibitor of KDM5A is F3358-0326.

5. The method of claim 1, wherein the small molecule inhibitor of KDM5A is F3385-1519.

6. The method of claim 1, wherein the small molecule inhibitor of KDM5A is 2,4-PDCA.

7. The method of claim 1, wherein the small molecule inhibitor of KDM5A is J11304.

* * * * *

UNITED STATES PATENT AND TRADEMARK OFFICE
CERTIFICATE OF CORRECTION

| | | |
|---|---|---|
| PATENT NO. | : 11,873,494 B2 | Page 1 of 1 |
| APPLICATION NO. | : 17/406441 | |
| DATED | : January 16, 2024 | |
| INVENTOR(S) | : Michael R. Green and Minggang Fang | |

It is certified that error appears in the above-identified patent and that said Letters Patent is hereby corrected as shown below:

On the Title Page

Column 2 Item (56) (Other Publications), Line 33, delete "inMethods" and insert -- Methods --.

In the Specification

Column 1, Line 12, delete "16/847,876," and insert -- 16/487,876, --.

In the Claims

In Claim 7, Column 35, Line 4, delete "J11304." and insert -- JIB04. --.

Signed and Sealed this
Twenty-seventh Day of August, 2024

Katherine Kelly Vidal
*Director of the United States Patent and Trademark Office*